(12) United States Patent
Ishiwata

(10) Patent No.: US 7,947,815 B2
(45) Date of Patent: May 24, 2011

(54) DIAZENYL ISOTHIAZOLO[3,4-B]PYRIDINES AS DYES

(75) Inventor: Yasuhiro Ishiwata, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 861 days.

(21) Appl. No.: 11/631,188

(22) PCT Filed: Jun. 29, 2005

(86) PCT No.: PCT/JP2005/012431
§ 371 (c)(1), (2), (4) Date: Mar. 29, 2007

(87) PCT Pub. No.: WO2006/004134
PCT Pub. Date: Jan. 12, 2006

(65) Prior Publication Data
US 2008/0027221 A1    Jan. 31, 2008

(30) Foreign Application Priority Data

Jun. 30, 2004  (JP) ................................. 2004-194866
Sep. 24, 2004  (JP) ................................. 2004-277895

(51) Int. Cl.
*C09B 29/039*  (2006.01)
*D06P 1/18*    (2006.01)

(52) U.S. Cl. ............ 534/765; 534/766; 534/767; 8/466; 8/662

(58) Field of Classification Search ................... 546/114; 514/301; 534/765
See application file for complete search history.

(56) References Cited

U.S. PATENT DOCUMENTS 4,524,124 A * 6/1985 Bergthaller et al. .......... 430/241
5,091,517 A   2/1992 Naef

FOREIGN PATENT DOCUMENTS

| DE | 23 54 686 A1 | 5/1975 |
|---|---|---|
| DE | 42 13 395 A1 | 10/1992 |
| EP | 0 132 577 A1 | 2/1985 |
| EP | 1 529 816 A1 | 5/2005 |
| EP | 1 849 454 A1 | 10/2007 |
| JP | 56-55455 A | 5/1981 |
| JP | 60-14243 A | 1/1985 |
| JP | 9-152703 A | 6/1997 |
| JP | 11-500781 A | 1/1999 |
| JP | 11-125888 A | 5/1999 |
| JP | 2000-280630 A | 10/2000 |
| JP | 2001-201834 A | 7/2001 |
| JP | 2002-3410 A | 1/2002 |
| JP | 2002-80746 A | 3/2002 |

OTHER PUBLICATIONS

Raber, L. (Chem. & Eng. News, 2000, 78(11), p. 52 (1 of 3).*
Sayer, T.S.B., "Synthesis of Novel Aminoisothiazolopyridines", Dyes and Pigments, 1982, vol. 3, pp. 123-131.

* cited by examiner

*Primary Examiner* — Susanna Moore
(74) *Attorney, Agent, or Firm* — Sughrue Mion, PLLC

(57) ABSTRACT

An azo dye represented by the following formula (I):

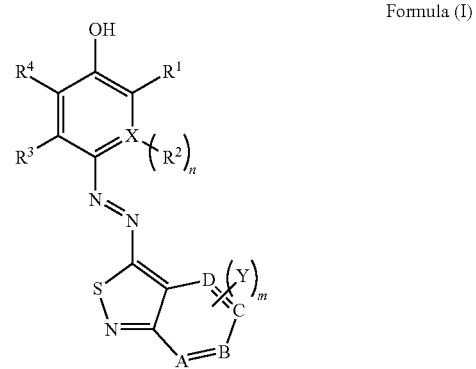

Formula (I)

wherein, in formula (I), $R^1$, $R^2$, $R^3$, and $R^4$ each independently represent a hydrogen atom, an aliphatic group, an aryl group, a halogen atom, an acyl group, a cyano group, an acylamino group, an aliphatic oxycarbonyl group, an aryloxycarbonyl group, a carbamoyl group, an aliphatic sulfonyl group, an arylsulfonyl group, a sulfamoyl group, an aliphatic oxycarbonylamino group, an aryloxycarbonylamino group, a sulfo group, a carboxyl group, a carbamoylamino group, a sulfamoylamino group, or an aliphatic- or aromatic-sulfonylamino group, wherein $R^1$ and $R^2$ and/or $R^3$ and $R^4$ may be combined with each other to form a five- or six-membered aromatic ring or non-aromatic ring; X represents a carbon atom or a nitrogen atom, wherein n is 0 when X is a nitrogen atom and n is 1 when X is a carbon atom; A, B, C, and D each represent a carbon atom or a nitrogen atom, provided that at least one of A, B, C and D represents a nitrogen atom; Y represents a substituent; and m denotes an integer from 0 to 3.

6 Claims, 6 Drawing Sheets

DIAZENYL ISOTHIAZOLO[3,4-B]PYRIDINES AS DYES

TECHNICAL FIELD

The present invention relates to a novel sulfur- and nitrogen-containing heterocyclic azo dye.

BACKGROUND ART

Many azo dyes have absorption of various visible lights and have been therefore conventionally utilized as dyes in various fields. These azo dyes have come to be utilized in various fields, for example, coloring of synthetic resins, printing inks, dyes for sublimation type heat-sensitive transfer material, ink jet inks, and color filter dyes. An absorption spectrum is among the important properties required for azo dyes. The hue of a dye has a large influence on the tint, feeling, and the like of a material colored with the dye, and has a large visual effect. Therefore, studies have been made as to the absorption spectrums of dyes, for a long time. A review thereof is described in "Dyes and Pigments" (1982), vol. 3, pp. 123-131, and it has a detailed explanation.

Recently, the mainstream of image recording materials has been shifted to color image materials, and the applications of dyes have also been diversified. Specifically, dyes are often utilized in recording materials for ink jet systems, recording materials for heat-sensitive transfer systems, recording materials for electrophotographic systems, silver halide light-sensitive materials utilizing transfer systems, and printing inks. Color filters are used to record and reproduce a color image, in imaging devices such as CCDs in the case of photographing devices and in LCDs and PDPs in the case of displays. In these color image recording materials and color filters, colorants (dyes and pigments) having three primary colors in the so-called additive color mixing method or subtractive color mixing method are used, to reproduce and record a full-color image. However, the current situation is still in lack of colorant which has absorbing properties enabling the realization of a desirable color reproducing range, and which can stand to various working conditions and environmental conditions, giving a good hue and high fastness. Therefore, there is a strong demand for improvement.

In the meantime, as regards cyan type azo dyes, dyes are known which use benzoisothiazole as the azo part, under the idea that the absorption wavelength can be made longer without using a nitro group (for example, each publication of JP-T-11-500781 ("JP-T" means searched and published International patent publication) and JP-A-2001-201834 ("JP-A" means unexamined published Japanese patent application)). However, the azo dyes used in these patents have insufficient heat resistance and light fastness, and it is therefore desired to further improve these dyes. It is also commonly required that an azo dye used in each application, has absorbing properties desirable in color reproduction, high fastness in working circumstances, and a large molar extinction coefficient.

Conventionally, azo dyes having, as the azo component, an isothiazole condensed with a five- to six-membered heterocycle are disclosed in each publication of JP-A-56-55455, JP-A-60-14243, JP-A-11-125888, and JP-A-2000-280630. Any of these dyes does not have satisfactory hue, fastness, and molecular extinction coefficient. There are also the descriptions on a method of synthesizing azo dyes having, as the azo component, an isothiazole condensed with a six-membered heterocycle, in "Dyes and Pigments" (1982), vol. 3, pp. 123-131. However, these dyes do not have satisfactory hue, molecular extinction coefficient, and the like.

Other and further features and advantages of the invention will appear more fully from the following description, with taken in connection with the accompanying drawings.

DISCLOSURE OF INVENTION

The present invention provides an azo dye with a novel structure, having a good hue, fastness, and a high molecular extinction coefficient.

The inventors of the present invention have made earnest studies and, as a result, found that a specific nitrogen-containing heterocyclic azo dye has a good hue and high fastness to light and heat, and completed the present invention based on these findings.

The present invention provides the following measures.

(1) An azo dye represented by the following formula (I):

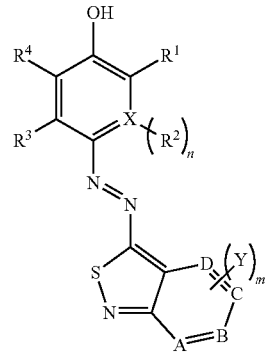

Formula (I)

wherein, in formula (I), $R^1$, $R^2$, $R^3$, and $R^4$ each independently represent a hydrogen atom, an aliphatic group, an aryl group, a halogen atom, an acyl group, a cyano group, an acylamino group, an aliphatic oxycarbonyl group, an aryloxycarbonyl group, a carbamoyl group, an aliphatic sulfonyl group, an arylsulfonyl group, a sulfamoyl group, an aliphatic oxycarbonylamino group, an aryloxycarbonylamino group, a sulfo group, a carboxyl group, a carbamoylamino group, a sulfamoylamino group, or an aliphatic- or aromatic-sulfonylamino group, wherein $R^1$ and $R^2$ and/or $R^3$ and $R^4$ may be combined with each other to form a five- or six-membered aromatic ring or non-aromatic ring; X represents a carbon atom or a nitrogen atom, wherein n is 0 when X is a nitrogen atom and n is 1 when X is a carbon atom; A, B, C, and D each represent a carbon atom or a nitrogen atom, provided that at least one of A, B, C and D represents a nitrogen atom; Y represents a substituent; and m denotes an integer from 0 to 3.

(2) A dye represented by the following formula (IA):

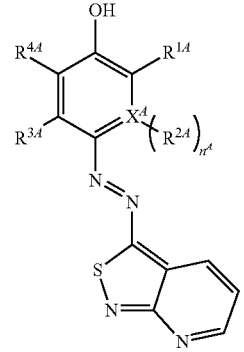

Formula (IA)

wherein, in formula (IA), $R^{1A}$, $R^{2A}$, $R^{3A}$, and $R^{4A}$ each independently represent a hydrogen atom, an aliphatic group, an aryl group, a halogen atom, an acyl group, a cyano group, an acylamino group, an aliphatic oxycarbonyl group, an aryloxycarbonyl group, a carbamoyl group, an aliphatic sulfonyl group, an arylsulfonyl group, a sulfamoyl group, an aliphatic oxycarbonylamino group, an aryloxycarbonylamino group, a sulfo group, a carboxyl group, a carbamoylamino group, a sulfamoylamino group, or an aliphatic- or aromatic-sulfonylamino group, wherein $R^{1A}$ and $R^{2A}$ and/or $R^{3A}$ and $R^{4A}$ may be combined with each other to form a five- or six-membered aromatic ring or non-aromatic ring; $X^A$ represents a carbon atom or a nitrogen atom, wherein $n^A$ is 0 when $X^A$ is a nitrogen atom and $n^A$ is 1 when $X^A$ is a carbon atom.

(3) An azo dye represented by the following formula (IB):

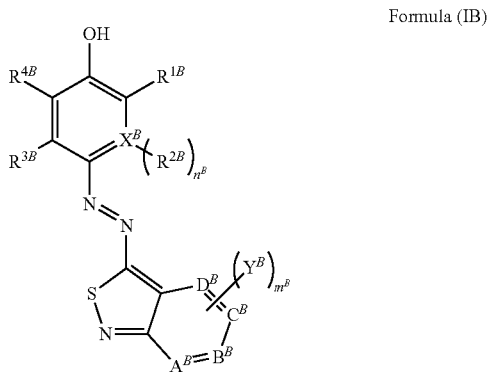

Formula (IB)

wherein, in formula (IB), $R^{1B}$, $R^{2B}$, $R^{3B}$, and $R^{4B}$ each independently represent a hydrogen atom, an aliphatic group, an aryl group, a halogen atom, an acyl group, a cyano group (a nitrile group), an acylamino group, an aliphatic oxycarbonyl group, an aryloxycarbonyl group, a carbamoyl group, an aliphatic sulfonyl group, an arylsulfonyl group, a sulfamoyl group, an aliphatic oxycarbonylamino group, an aryloxycarbonylamino group, a sulfo group, a carboxyl group, a carbamoylamino group, a sulfamoylamino group, or an aliphatic- or aromatic-sulfonylamino group, wherein $R^{1B}$ and $R^{2B}$ and/or $R^{3B}$ and $R^{4B}$ may be combined with each other to form a five- or six-membered aromatic ring or non-aromatic ring; $X^B$ represents a carbon atom or a nitrogen atom, wherein $n^B$ is 0 when $X^B$ is a nitrogen atom and $n^B$ is 1 when $X^B$ is a carbon atom; $A^B$, $B^B$, $C^B$, and $D^B$ each represent a carbon atom or a nitrogen atom, provided that at least one of $A^B$, $B^B$, $C^B$ and $D^B$ represents a nitrogen atom; $Y^B$ represents a substituent; and $m^B$ denotes an integer from 0 to 3; provided that $M^B$ is an integer of 1 or more when $A^B$ represents a nitrogen atom and $B^B$, $C^B$, and $D^B$ each represent a carbon atom.

Hereinafter, among the compounds represented by the aforementioned formula (I), the azo dyes represented by formula (IA) are referred to as the first embodiment of the present invention.

Further, among the compounds represented by the aforementioned formula (I), the azo dyes represented by formula (IB) are referred to as the second embodiment of the present invention.

Herein, the present invention means to include all of the above first and second embodiments, unless otherwise specified.

BEST MODE FOR CARRYING OUT INVENTION

Figure 1:
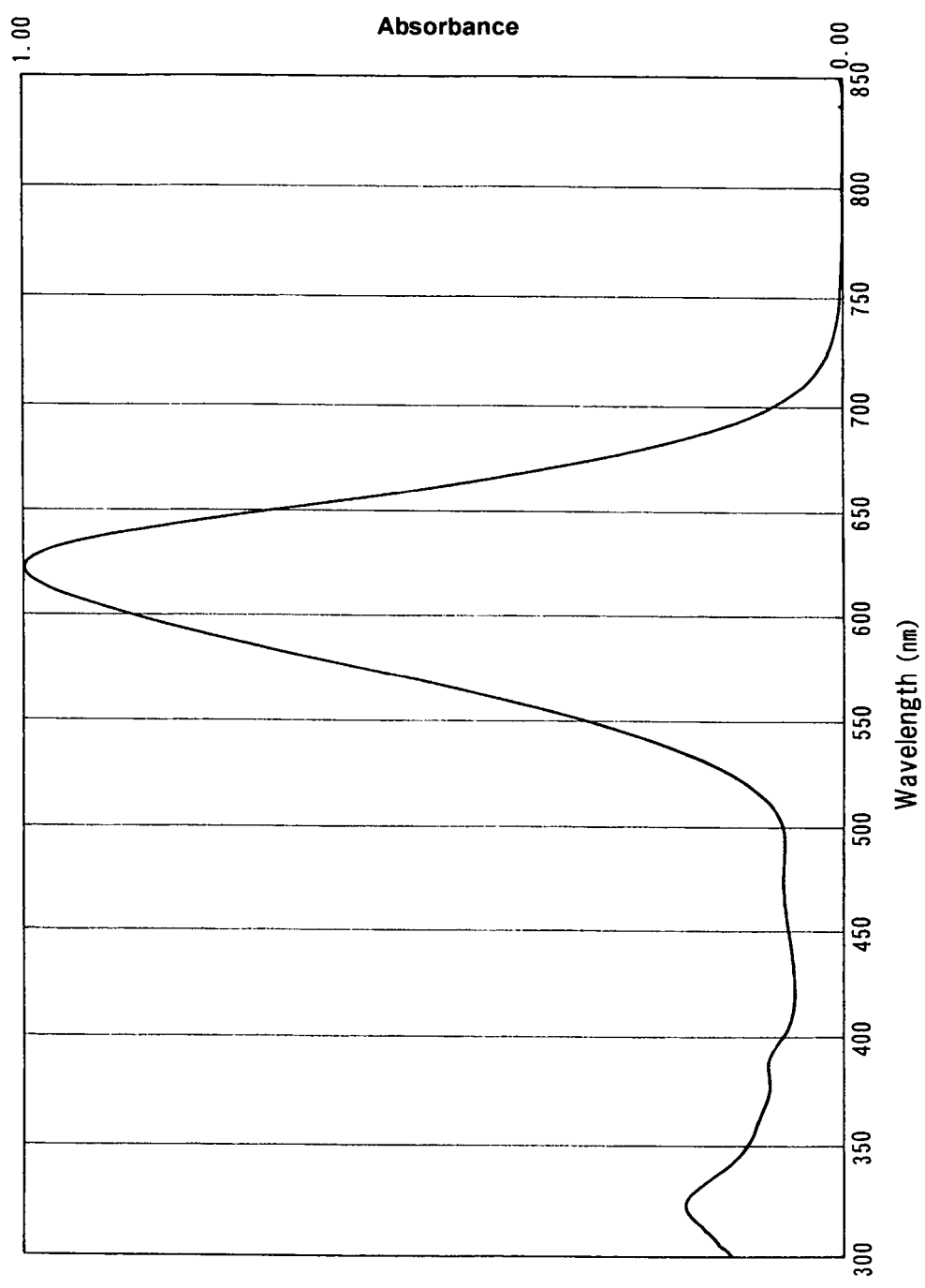
FIG. 1 is an absorption spectrum of the dye synthesized in Example 1-1 (solvent: N,N-dimethylformamide)

The present invention will be explained in detail.
As to the term "aliphatic" in the present specification, the aliphatic part thereof may be straight-chain, branched-chain, or cyclic, and saturated or unsaturated. For example, the aliphatic group represents an alkyl group, an alkenyl group, or an alkynyl group, which may be unsubstituted or may have a substituent. The "aryl" may be a single ring or a condensed ring, and may be unsubstituted or may have a substituent.

The compound represented by formula (I) will be explained in detail below.

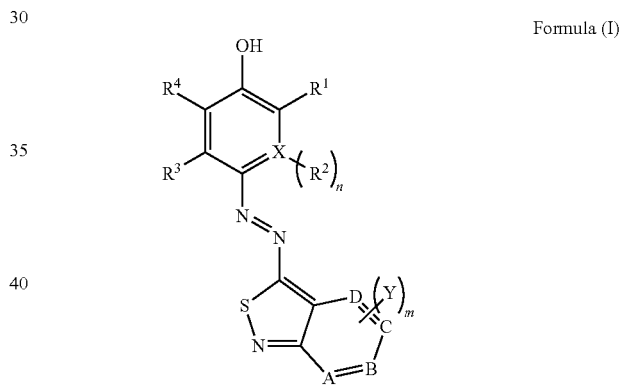

Formula (I)

In formula (I), $R^1$, $R^2$, $R^3$, and $R^4$ each independently represent a hydrogen atom, an aliphatic group, an aryl group, a halogen atom, an acyl group, a cyano group, an acylamino group, an aliphatic oxycarbonyl group, an aryloxycarbonyl group, a carbamoyl group, an aliphatic sulfonyl group, an arylsulfonyl group, a sulfamoyl group, an aliphatic oxycarbonylamino group, an aryloxycarbonylamino group, a sulfo group, a carboxyl group, a carbamoylamino group, a sulfamoylamino group, or an aliphatic- or aromatic-sulfonylamino group, wherein $R^1$ and $R^2$ and/or $R^3$ and $R^4$ may be combined with each other to form a five- or six-membered aromatic ring or non-aromatic ring; X represents a carbon atom or a nitrogen atom, wherein n is 0 when X is a nitrogen atom and n is 1 when X is a carbon atom; A, B, C, and D each represent a carbon atom or a nitrogen atom, provided that at least one of A, B, C and D represents a nitrogen atom; Y represents a substituent; and m denotes an integer from 0 to 3.

Among the groups designed by $R^1$ to $R^4$, the aliphatic group may have a substituent, may be saturated or unsaturated, preferably has a total of 1 to 15 carbon atoms, and is, for example, methyl, ethyl, vinyl, allyl, ethynyl, isopropenyl, or 2-ethylhexyl. The aryl group may have a substituent, preferably has a total of 6 to 16 carbon atoms, and is, for example, phenyl, 4-nitrophenyl, 2-nitrophenyl, 2-chlorophenyl, 2,4-dichlorophenyl, 2,4-dimethylphenyl, 2-methylphenyl, 4-methoxyphenyl, 2-methoxyphenyl, or 2-methoxycarbonyl-4-nitrophenyl. The acyl group may be aromatic or aliphatic, preferably has a total of 2 to 15 carbon atoms, and is, for example, acetyl, pivaloyl, or benzoyl. The aliphatic oxycarbonyl group may have a substituent, may be saturated or unsaturated, preferably has a total of 2 to 16 carbon atoms, and is, for example, methoxycarbonyl or butoxycarbonyl. The aryloxycarbonyl group may have a substituent, preferably has a total of 7 to 17 carbon atoms, and is, for example, phenoxycarbonyl. The carbamoyl group may have a substituent, preferably has a total of 1 to 12 carbon atoms, and is, for example, carbamoyl or dimethylcarbamoyl. The aliphatic sulfonyl group may have a substituent, may be saturated or unsaturated, preferably has a total of 1 to 15 carbon atoms, and is, for example, methanesulfonyl, butanesulfonyl, or methoxyethanesulfonyl. The arylsulfonyl group may have a substituent, preferably has a total of 6 to 16 carbon atoms, and is, for example, phenylsulfonyl, 4-t-butylphenylsulfonyl, 4-toluenesulfonyl, or 2-toluenesulfonyl. The sulfamoyl group may have a substituent, preferably has a total of 0 to 12 carbon atoms, and represents, for example, sulfamoyl or dimethylsulfamoyl.

The acylamino group may have a substituent, preferably has a total of 1 to 8 carbon atoms, and is, for example, an acetylamino group, a propionylamino group, a chloroacetylamino group, or a benzoylamino group. The aliphatic oxycarbonylamino group may have a substituent, preferably has a total of 2 to 6 carbon atoms, and is, for example, a methoxycarbonylamino group, an ethoxycarbonylamino group, or a methoxyethoxycarbonylamino group. The aryloxycarbonylamino group may have a substituent, preferably has a total of 7 to 10 carbon atoms, and is, for example, a phenoxycarbonylamino group, or a p-chlorophenoxycarbonylamino group. The carbamoylamino group may have a substituent, preferably has a total of 1 to 8 carbon atoms, and is, for example, a monomethylaminocarbonylamino group, a dimethylaminocarbonylamino group, a bis-(2-methoxyethyl)aminocarbonylamino group, a monoethylaminocarbonylamino group, a diethylaminocarbonylamino group, or a N-phenyl-N-methylaminocarbonylamino group. The sulfamoylamino group may have a substituent, preferably has a total of 0 to 8 carbon atoms and more preferably 1 to 8 carbon atoms, and is, for example, a sulfamoylamino group, a N-ethylsulfamoylamino group, or a N,N-dimethylsulfamoylamino group. The aliphatic- or aromatic-sulfonylamino group may have a substituent, preferably has a total of 1 to 12 carbon atoms, and is, for example, a methanesulfonylamino group, an ethanesulfonylamino group, a chloromethanesulfonylamino group, a propanesulfonylamino group, a butanesulfonylamino group, a n-octanesulfonylamino group, a n-dodecanesulfonylamino group, a benzenesulfonylamino group, 3-mesylaminobenzenesulfonylamino group, or a 4-methylbenzenesulfonylamino group.

Examples of the substituent which the groups designated by $R^1$, $R^2$, $R^3$, and $R^4$ may have include an aliphatic group, an aryl group, a halogen atom, an acyl group, a cyano group, an acylamino group, an aliphatic oxycarbonyl group, an aryloxycarbonyl group, a carbamoyl group, an aliphatic sulfonyl group, an arylsulfonyl group, a sulfamoyl group an aliphatic oxycarbonylamino group, an aryloxycarbonylamino group, a sulfo group, a carboxyl group, a carbamoylamino group, a sulfamoylamino group, or an aliphatic- or aromatic-sulfonylamino group.

Y represents a hydrogen atom or a substituent. Examples of the substituent include, though not limited to, those described for $R^1$, $R^2$, $R^3$ and $R^4$. Preferable examples of the substituent include a halogen atom, an alkyl group, a cyano group, an alkoxy group, an alkylthio group, an alkyl- or aryl-sulfonylamino group, a sulfamoyl group, an alkylsulfonyl group, an arylsulfonyl group, an acyl group, an alkoxycarbonyl group, and a carbamoyl group.

The synthesis of the dye of the present invention can be made by converting an amino body of a diazo component into a diazo compound, and then by coupling the resulting diazo compound with a phenol coupler.

This method itself is known and may be carried out according to the descriptions of, for example, each publication of JP-A-2003-342139 and JP-A-2000-248188.

The compound represented by formula (IA) according to the present invention, which is the first embodiment of the compound (also referred to as a dye) represented by formula (I), will be explained in more detail.

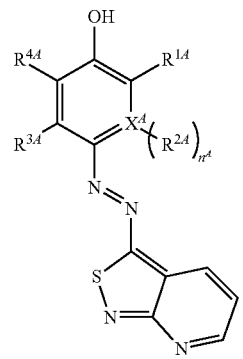

Formula (IA)

$R^{1A}$, $R^{2A}$, $R^{3A}$, $R^{4A}$, $X^A$, and $n^A$ in formula (IA) have the same meanings as $R^1$, $R^2$, $R^3$, $R^4$, X, and n in formula (I) respectively and each preferable range is also the same.

$R^{1A}$ is preferably a halogen atom, a cyano group, a carbamoyl group, a sulfamoyl group, an acylamino group, an aliphatic oxycarbonyl amino group, a carbamoylamino group, an aliphatic- or aromatic-sulfonylamino group, or a sulfamoylamino group, more preferably a halogen atom, a cyano group, a carbamoyl group, or an acylamino group, still more preferably an acylamino group or a halogen atom, and most preferably a chlorine atom or a fluorine atom, from the viewpoint of the effect of the present invention.

$R^{2A}$ is preferably a halogen atom, a hydrogen atom, or an aliphatic group, more preferably a hydrogen atom or a halogen atom, and most preferably a hydrogen atom, from the viewpoint of the effect of the present invention.

$R^{3A}$ is preferably a hydrogen atom, a halogen atom, an acylamino group, an aliphatic oxycarbonylamino group, a carbamoylamino group, an aliphatic or aromatic sulfonylamino group, or a sulfamoylamino group, more preferably a hydrogen atom, a halogen atom, or an acylamino group, still more preferably a hydrogen atom or a halogen atom, and most preferably a hydrogen atom, from the viewpoint of the effect of the present invention.

$R^{4A}$ is preferably a halogen atom, a hydrogen atom, or an acylamino group, more preferably a hydrogen atom or an acylamino group, and most preferably a hydrogen atom, from the viewpoint of the effect of the present invention.

It is also preferable that $R^{3A}$ and $R^{4A}$ be combined with each other to form a benzene ring or a lactam ring.

$X^A$ is preferably a carbon atom in view of the effect of the present invention.

It is to be noted that the compound (a), which is an example of the amino body of diazo component for use in preparing the dye of the present invention, may be prepared using the following compound (d), which may be prepared from commercially available 2-aminonicotinic acid by a usual method, as a starting material according to the method described in the publication of JP-A-56-55455.

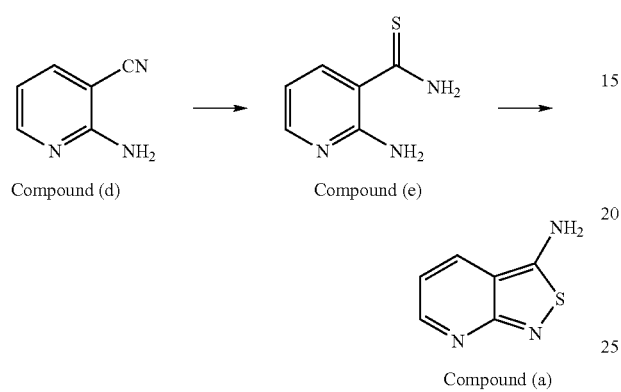

Compound (d)  Compound (e)

Compound (a)

Specific examples of the dye (dye-stuff) represented by the above formula (IA) will be shown below, however, these examples are not intended to be limiting of the present invention.

(D-1)

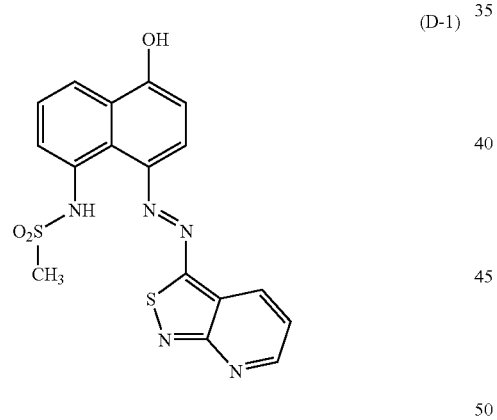

(D-2)

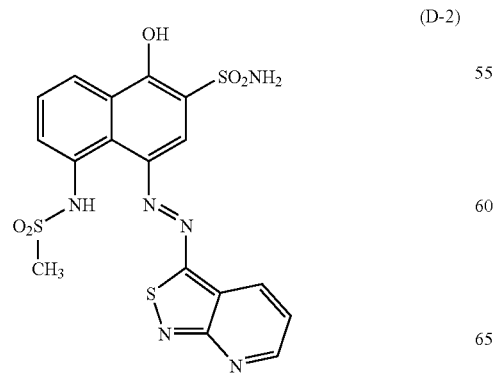

(D-3)

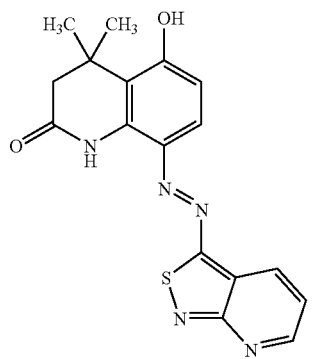

(D-4)

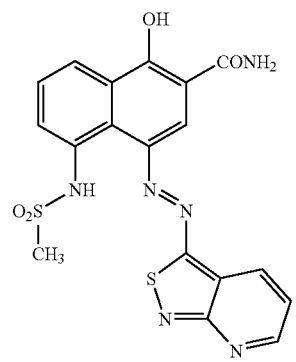

(D-5)

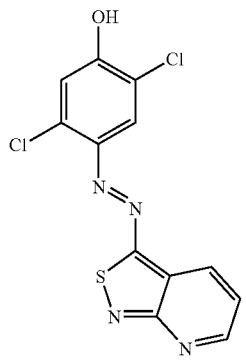

(D-6)

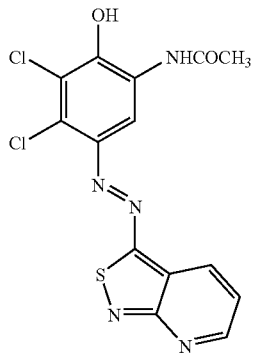

(D-7)
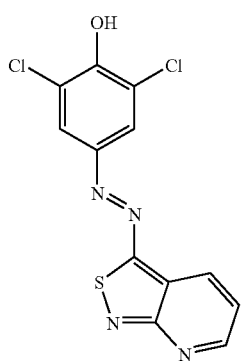
(D-8)
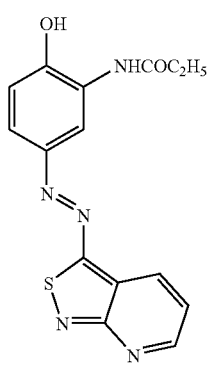
(D-9)
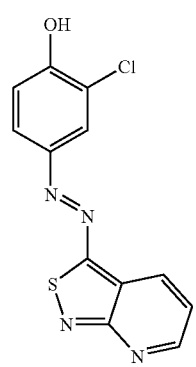
(D-10)
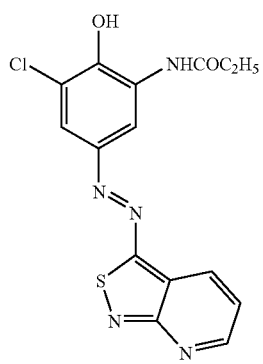
(D-11)
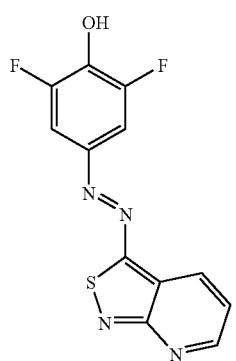
(D-12)
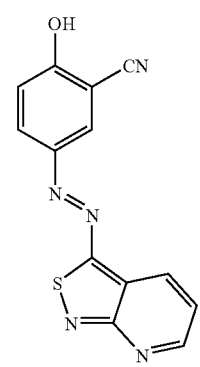
(D-13)
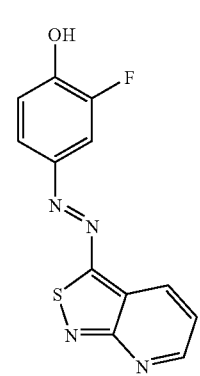
(D-14)
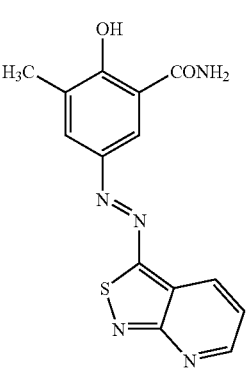

-continued
(D-15)
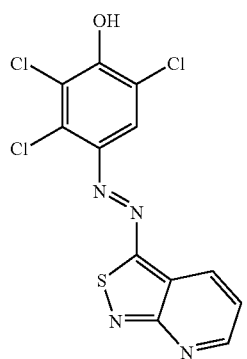
(D-16)
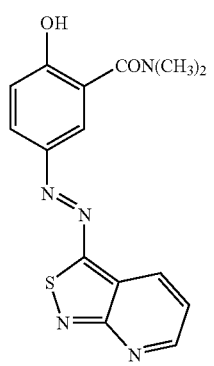
(D-17)
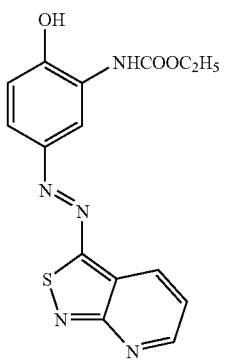
(D-18)
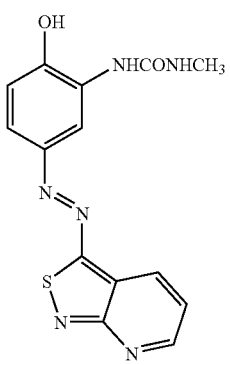
(D-19)
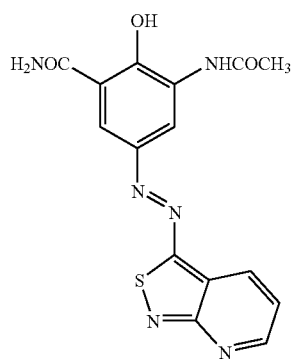
(D-20)
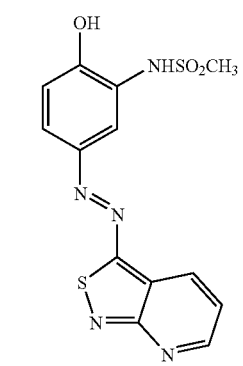
(D-21)
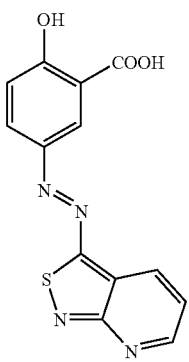
(D-22)
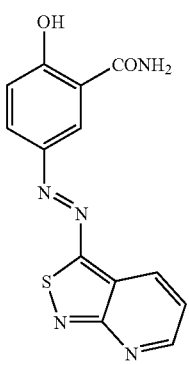

(D-23) 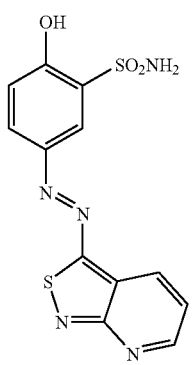
(D-24) 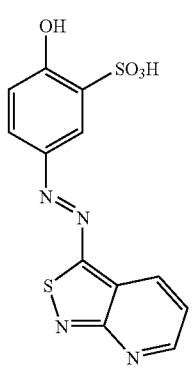
(D-25) 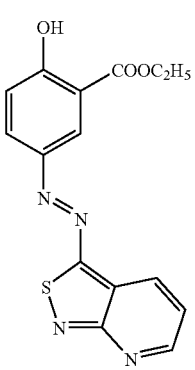
(D-26) 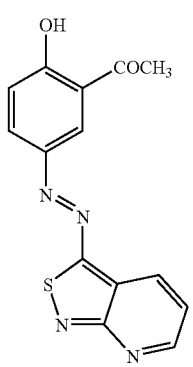
(D-27) 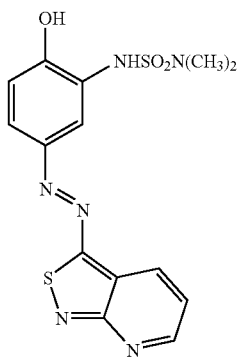
(D-28) 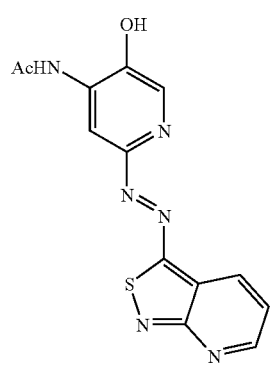
(D-29) 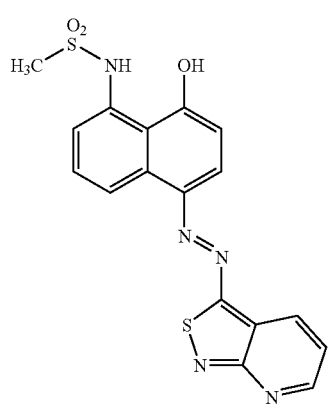
(D-30) 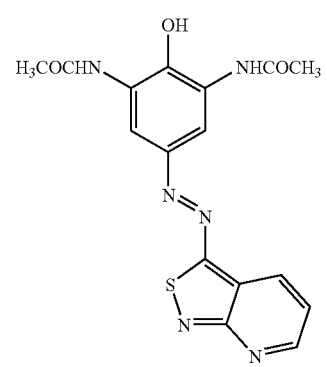

(D-31) 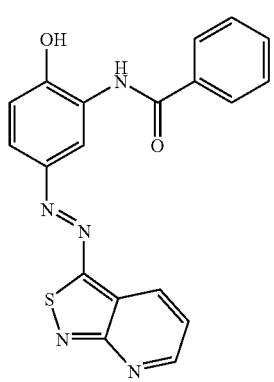
(D-32) 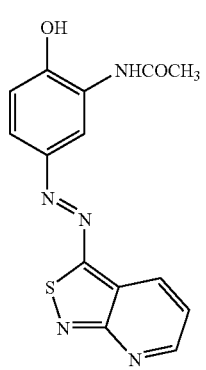
(D-33) 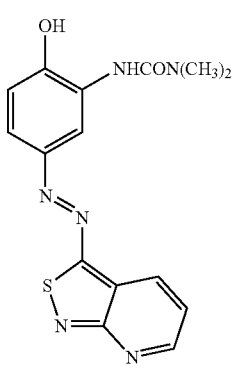
(D-34) 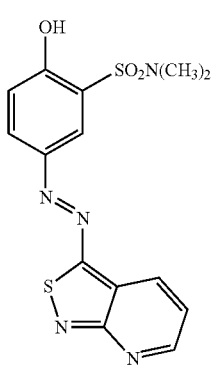
(D-35) 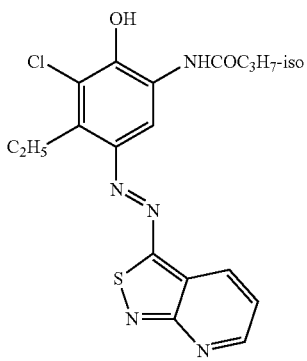
(D-36) 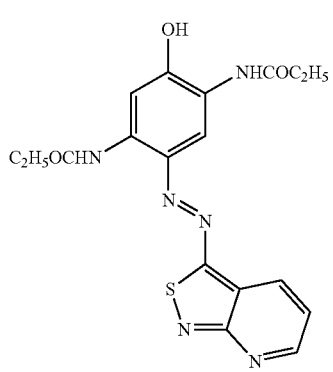
(D-37) 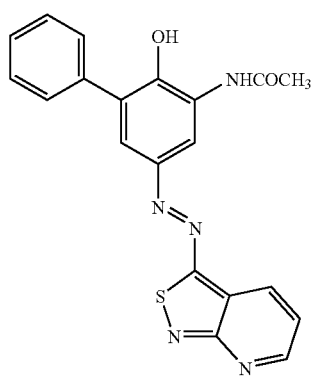
(D-38) 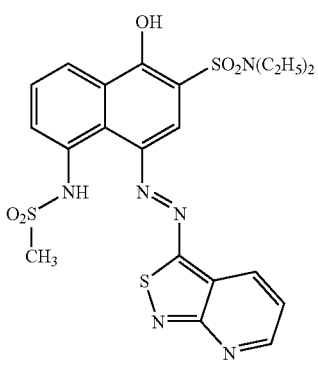

(D-39)
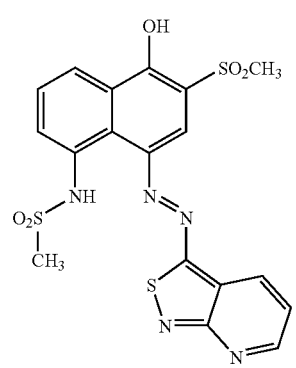
(D-40)
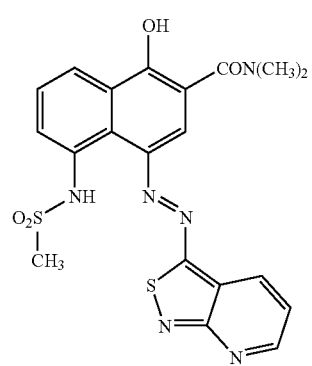
(D-41)
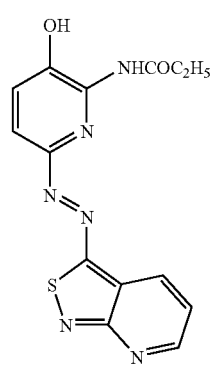
(D-42)
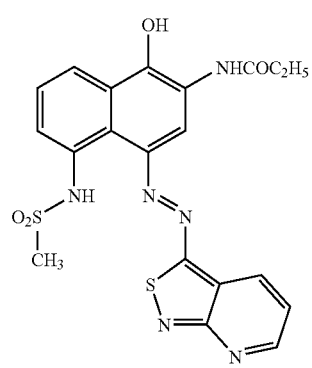
(D-43)
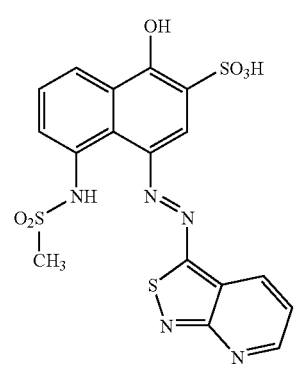
(D-44)
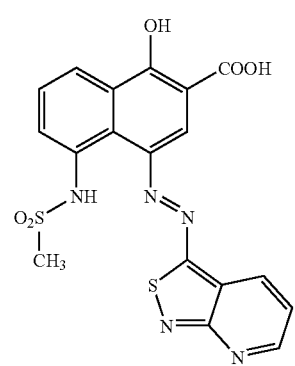
(D-45)
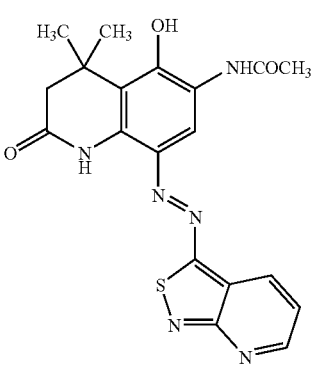
(D-46)
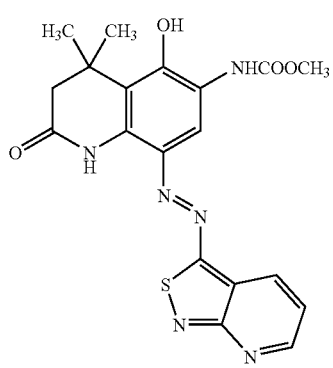

-continued (D-47)
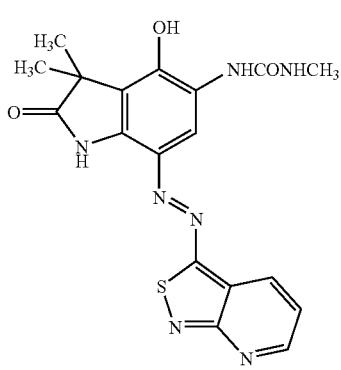

(D-48)
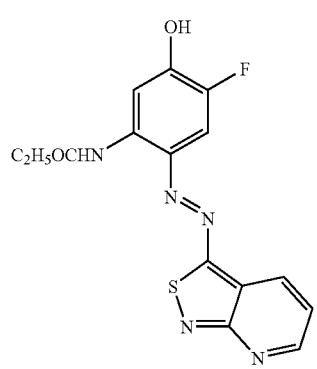

(D-49)
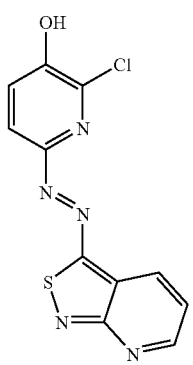

(D-50)
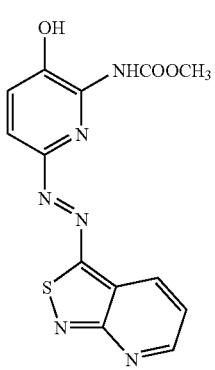

-continued (D-51)
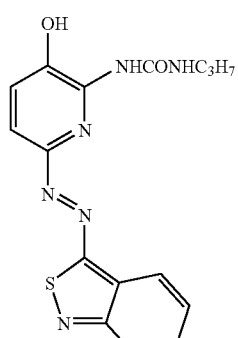

(D-52)
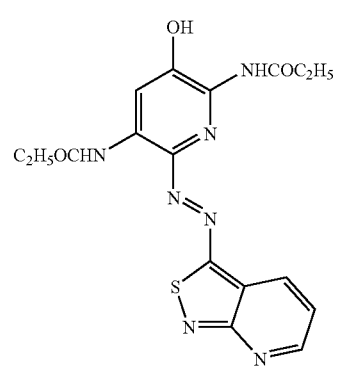

Many of the dyes exemplified above are dyes having absorption maximums at a wavelength range from 610 to 660 nm and molar extinction coefficients of 45,000 to 65,000.

The compound represented by formula (IB) according to the present invention, which is the second embodiment of the compound represented by formula (I), will be explained in more detail.

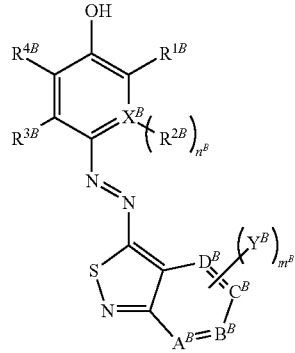

Formula (IB)

$R^{1B}, R^{2B}, R^{3B}, R^{4B}, X^B, n^B, A^B, B^B, C^B, D^B, Y^B$, and $m^B$ in formula (IB) have the same meanings as $R^1, R^2, R^3, R^4, X, n, A, B, C, D, Y$, and $m$ in formula (I) respectively and each preferable range is also the same.

$R^{1B}$ is preferably a halogen atom, a cyano group, a carbamoyl group, or an acylamino group, more preferably an acylamino group or a halogen atom, and most preferably a chlorine atom or a fluorine atom, from the viewpoint of obtaining more excellent effect.

$R^{2B}$ and $R^{3B}$ are preferably a halogen atom, a hydrogen atom, or an aliphatic group, more preferably a hydrogen atom or a halogen atom, and most preferably a hydrogen atom, from the viewpoint of obtaining more excellent effect.

$R^{4B}$ is preferably a halogen atom, a hydrogen atom, or an acylamino group, more preferably a hydrogen atom or an acylamino group, and most preferably a hydrogen atom, from the viewpoint of obtaining more excellent effect.

$Y^B$ is preferably a halogen atom, a cyano group, an alkyl group, or an alkylthio group, more preferably a cyano group, a halogen atom, or an alkylthio group, and most preferably a cyano group or an alkylthio group, from the viewpoint of obtaining more excellent effect.

$X^B$ is preferably a carbon atom from the viewpoint of obtaining more excellent effect.

Specific examples of the compound represented by the above formula (IB) will be shown below, however, these examples are not intended to be limiting of the present invention.

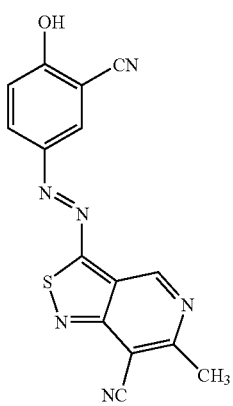
(A-1)

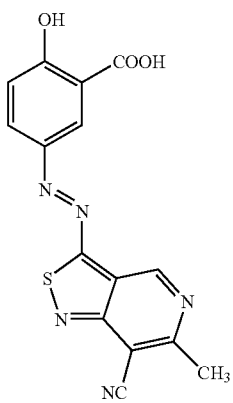
(A-2)

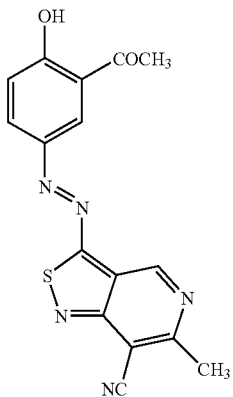
(A-3)

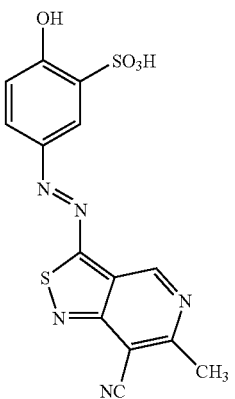
(A-4)

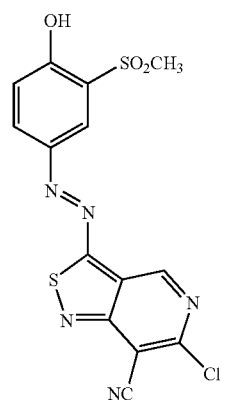
(A-5)

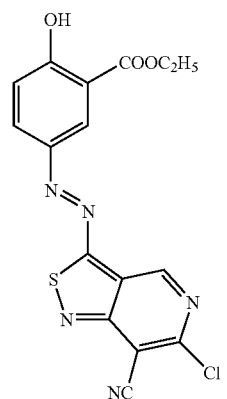
(A-6)

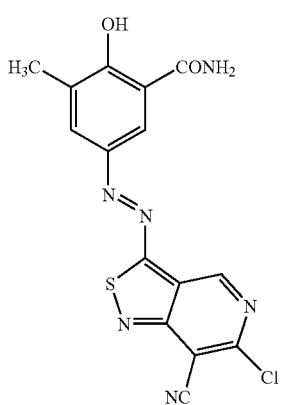
(A-7)

-continued
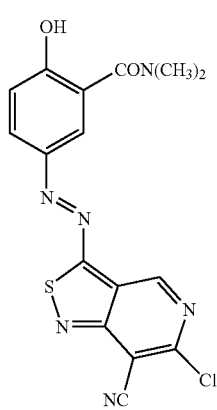 (A-8)
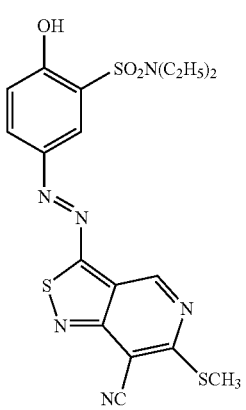 (A-9)
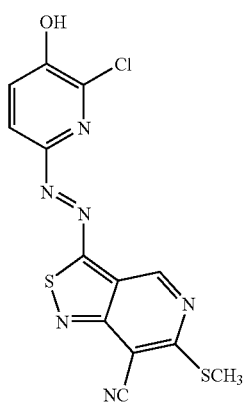 (A-10)
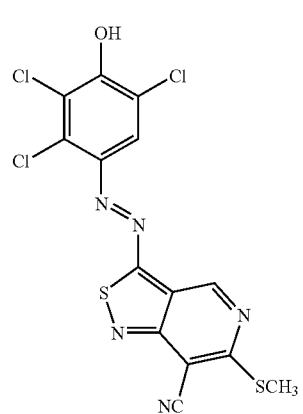 (A-11)
-continued
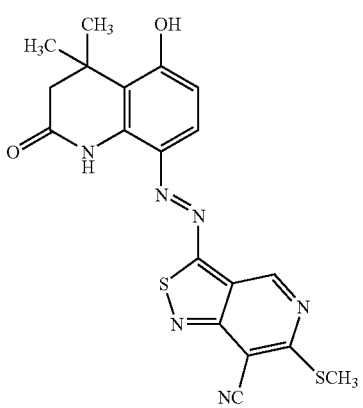 (A-12)
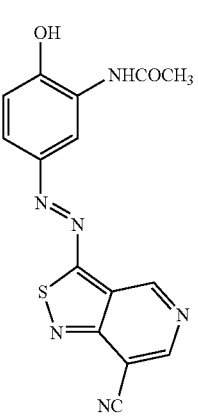 (A-13)
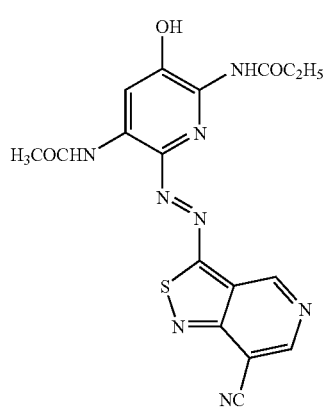 (A-14)
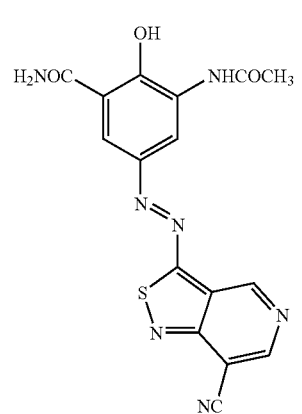 (A-15)

-continued
(A-16)
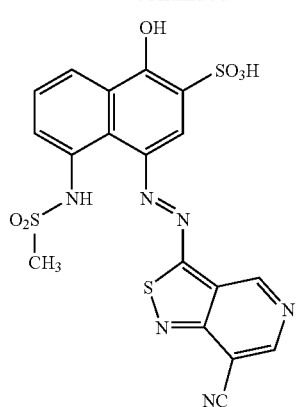
(A-17)
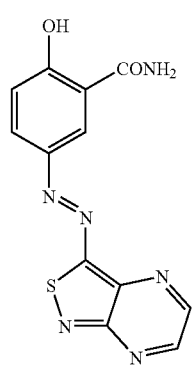
(A-18)
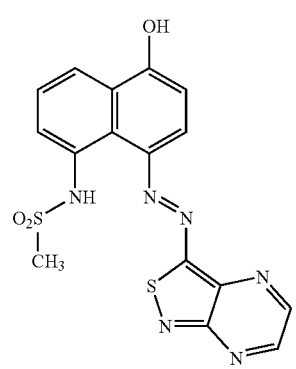
(A-19)
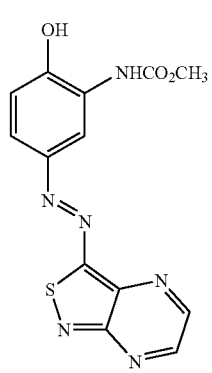
-continued
(A-20)
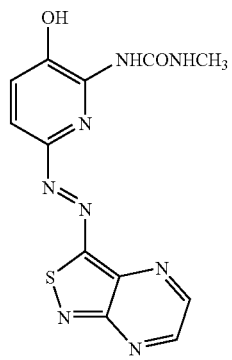
(A-21)
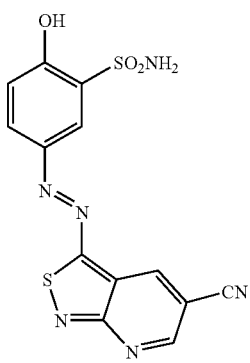
(A-22)
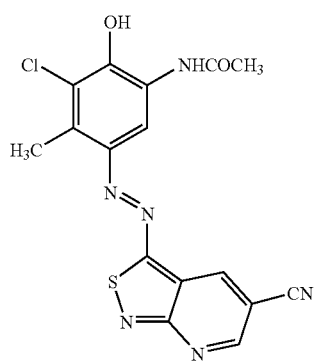
(A-23)
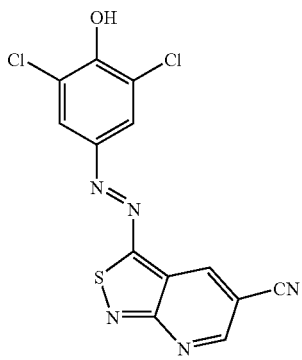

(A-24) 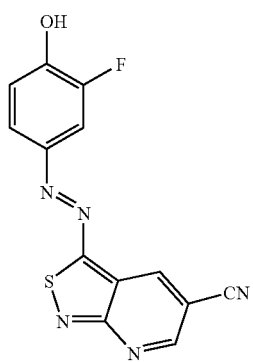
(A-25) 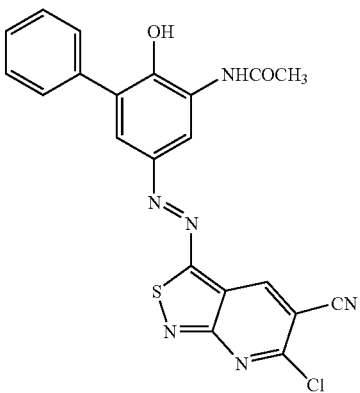
(A-26) 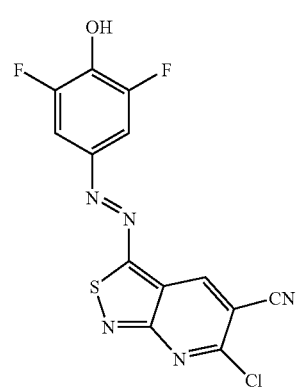
(A-27)
(A-28) 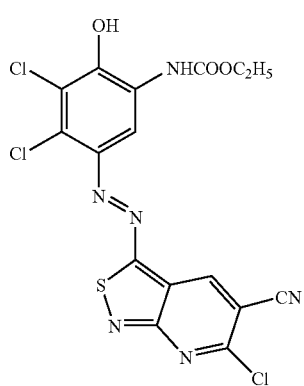
(A-29) 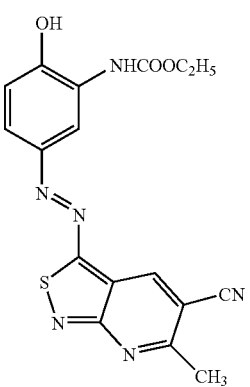
(A-30) 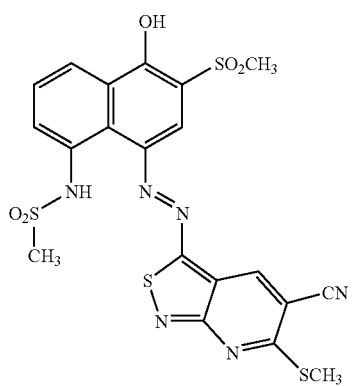
(A-31) 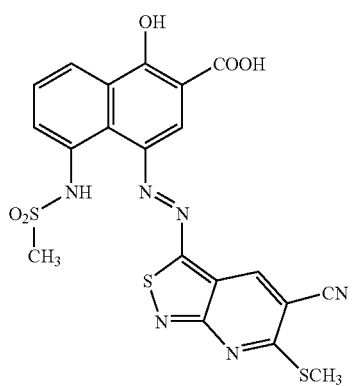

(A-32)
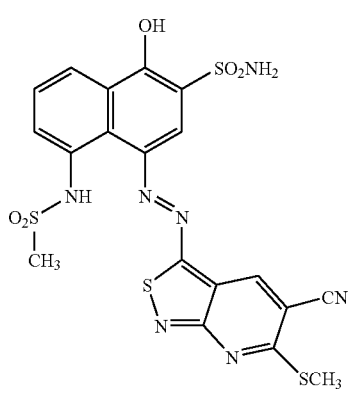
(A-33)
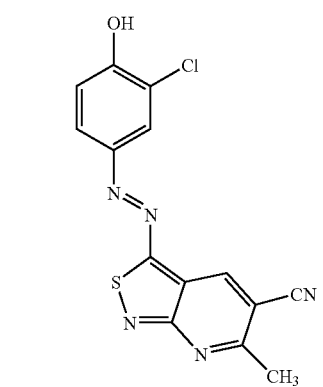
(A-34)
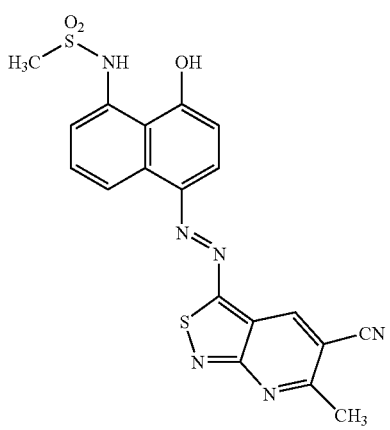
(A-35)
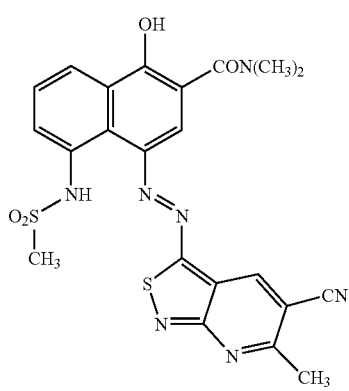
(A-36)
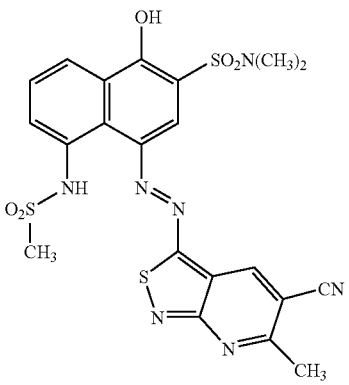
(A-37)
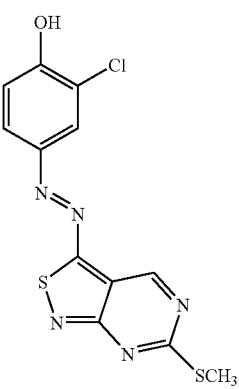
(A-38)
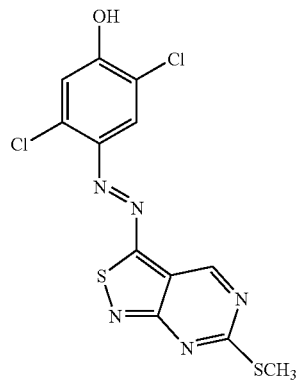
(A-39)
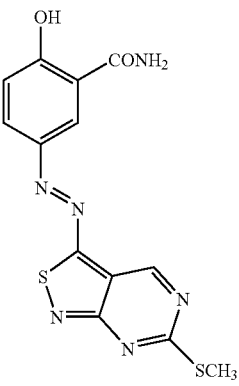

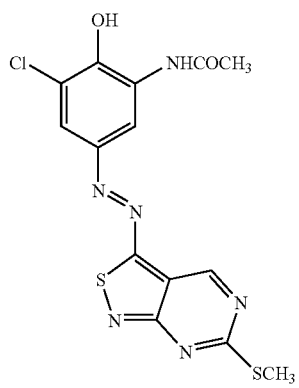
(A-40)
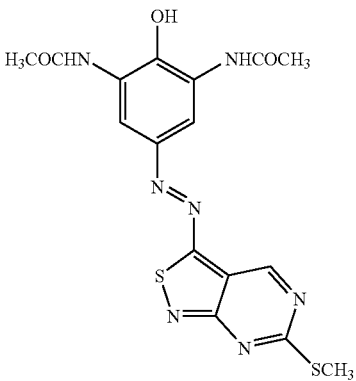
(A-44)
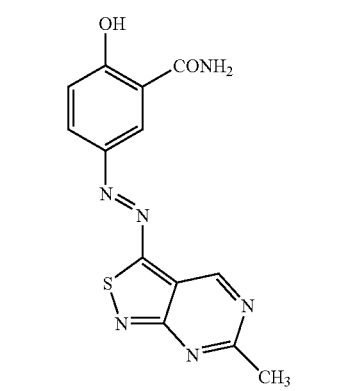
(A-45)
(A-41)
(A-42)
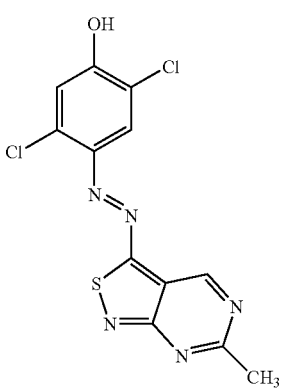
(A-46)
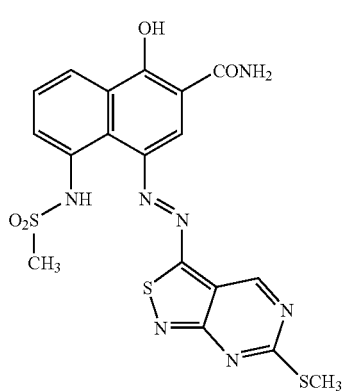
(A-43)
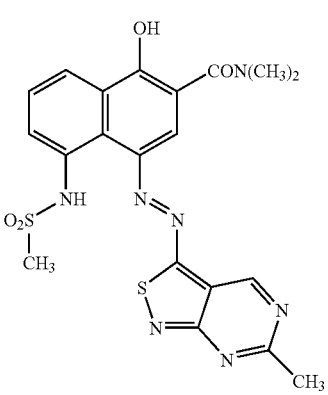
(A-47)

-continued
(A-48)
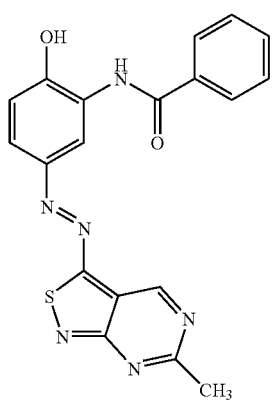
(A-49)
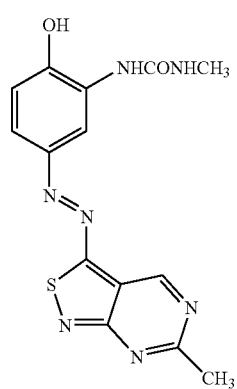
(A-50)
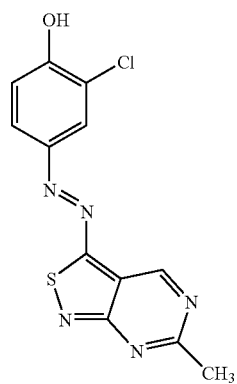
(A-51)
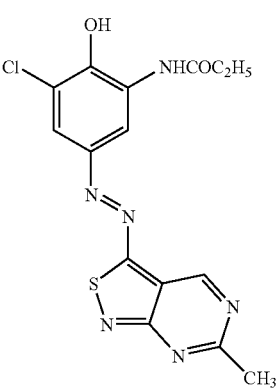
-continued
(A-52)
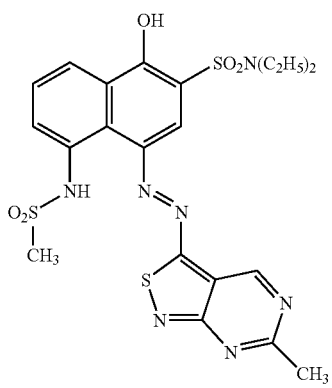
(A-53)
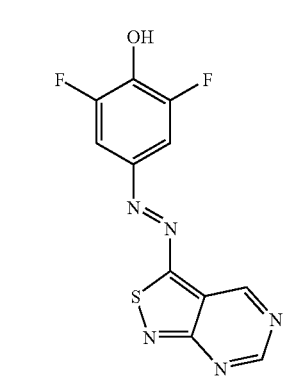
(A-54)
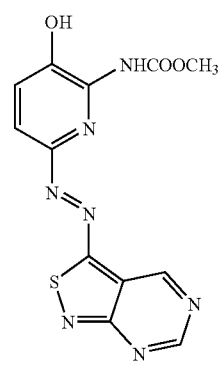
(A-55)
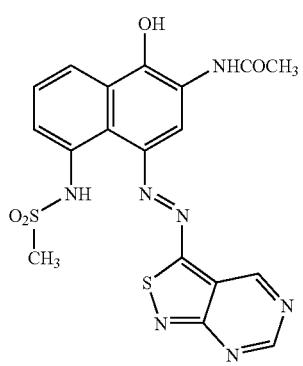

(A-56) 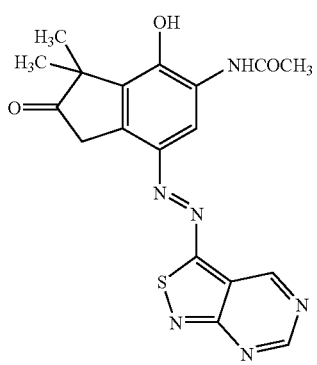
(A-57) 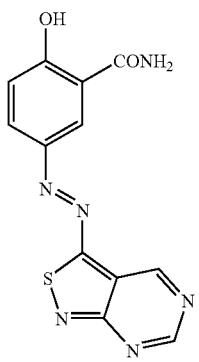
(A-58) 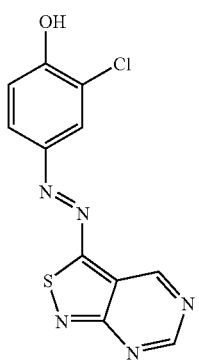
(A-59) 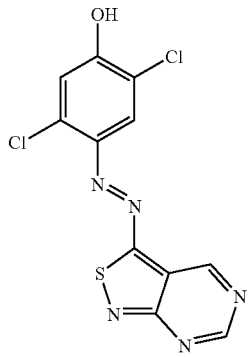
(A-60) 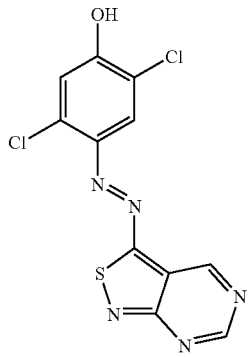
(A-61) 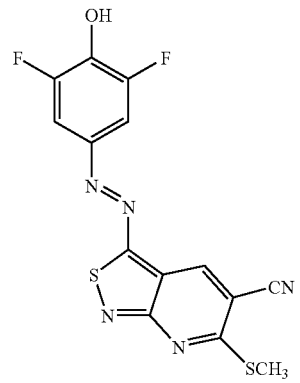
(A-62) 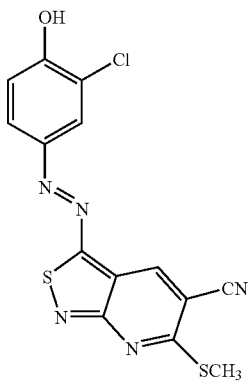
(A-63) 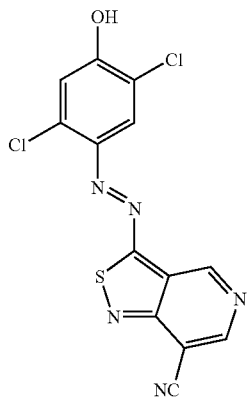

(A-64)
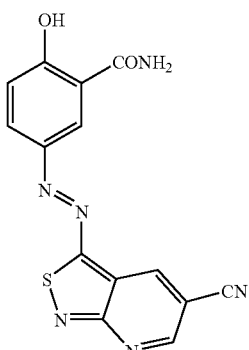

(A-65)
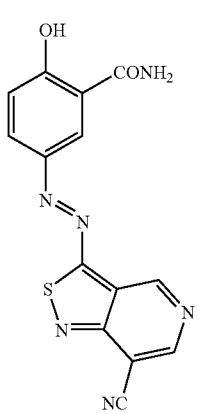

(A-66)
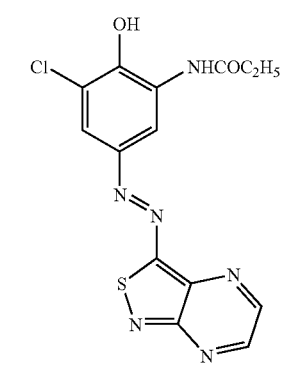

(A-67)
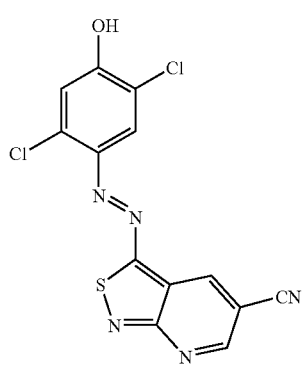

(A-68)
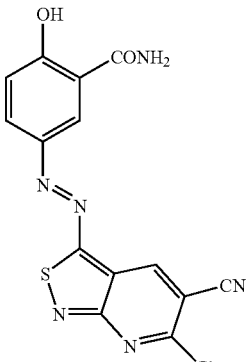

Many of the dyes exemplified above are dyes having absorption maximums at a wavelength range from 610 to 660 nm and molar extinction coefficients of 50,000 to 70,000.

The azo dye (azo dye-stuff) of the present invention is a novel dye which has excellent hue and has sufficient fastness to light, heat, humidity, and active gases in the environment, and has a high molar extinction coefficient.

The present invention will be described in more detail based on the following examples, but the invention is not intended to be limited thereto.

EXAMPLES

Example 1-1

Synthesis of the Exemplified Compound D-9

The exemplified compound (D-9) was prepared in the following method.

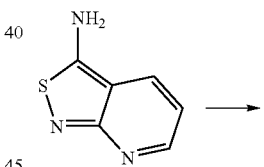

Compound(a)

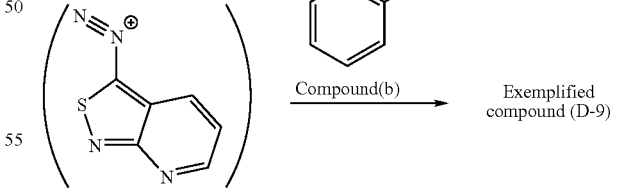

15.1 g (0.1 mol) of the compound (a) was suspended in 300 ml of phosphoric acid. 8.3 g (0.12 mol) of sodium nitrite was gradually added to the mixture while maintaining the internal temperature of 5° C. or less, and the mixture was stirred for 30 minutes. 12.9 g (0.1 mol, manufactured by Tokyo kasei Kogyo Co., Ltd.) of the compound (b) dissolved in 100 ml of acetic acid was added to the reaction solution, and the mixture was stirred at 10° C. for 5 hours. 2 l of water was added to the reaction solution, which was then stirred for 1 hour. The precipitated crystals were collected by filtration and washed sufficiently with water. The obtained crystals were dried and purified by silica gel column chromatography. The purified crystals were subjected to crystallization using 400 ml of a mixed solvent of methanol/water (1/1, mixing ratio in ml) and then subjected to filtration to collect crystals. The crystals were then washed with 100 ml of the aforementioned mixed solvent and dried to obtain 8.7 g of the exemplified compound (D-9) of the present invention as black crystals (Yield: 29.9%). Melting point: 257 to 258° C.; absorption maximum λmax in DMF: 620.3 nm (ε: 47,200); pka value in DMF/water (1/1, volume ratio): 5.94. This dye had the absorption spectrum shown in FIG. 1 and had a good hue. As to the fastness of the dye, neither a reduction in density nor discoloration was observed in the test described in Example 1 in the publication of JP-A-2000-280630; thus the dye was stable and had excellent fastness to light and heat.

Example 1-2

Synthesis of the Exemplified Compound D-10

The exemplified compound (D-10) was prepared in the following method.

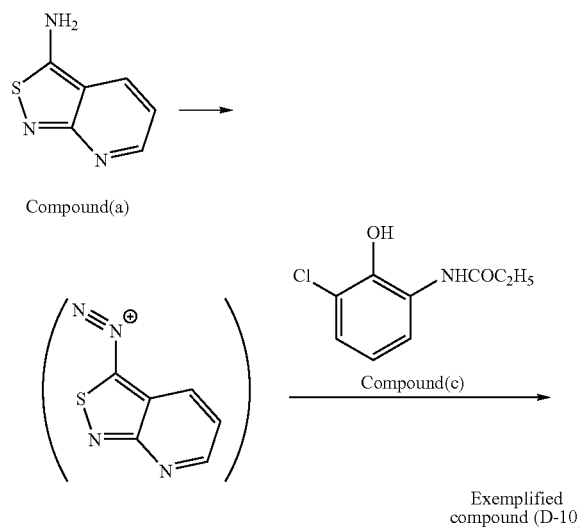

15.1 g (0.1 mol) of the compound (a) was suspended in 300 ml of phosphoric acid. 8.3 g (0.12 mol) of sodium nitrite was gradually added to the mixture while maintaining the internal temperature of 5° C. or less, and the mixture was stirred for 30 minutes. 20 g (0.1 mol) of the compound (c) dissolved in 150 ml of acetic acid was added to the reaction solution, and the mixture was stirred at 10° C. for 5 hours. 2 l of water was added to the reaction solution, which was then stirred for 1 hour. The precipitated crystals were collected by filtration and washed sufficiently with water. The obtained crystals were dried and purified by silica gel column chromatography. The purified crystals were subjected to crystallization using 400 ml of methanol and then subjected to filtration to collect crystals. The crystals were then washed with 100 ml of methanol and dried, to obtain 12 g (yield: 33.1%) of the exemplified compound (D-10) of the present invention as black crystals.

It is to be noted that the compound (c) used in the above synthesis was prepared from commercially available 2,3-dichloronitrobenzene (compound (f), manufactured by Aldrich Corporation), according to the following scheme, by converting the chlorine atom adjacent to the nitro group into a hydroxyl group and then reducing and acylating by a usual method.

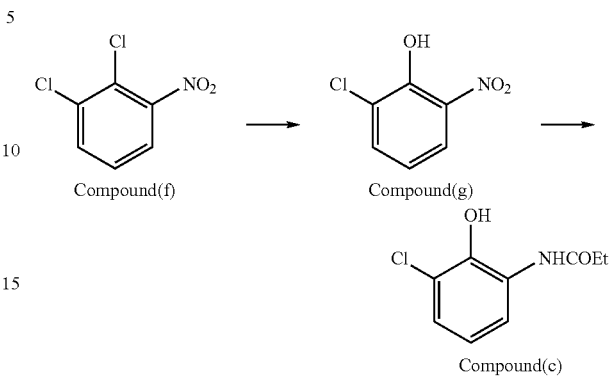

Figure 2:
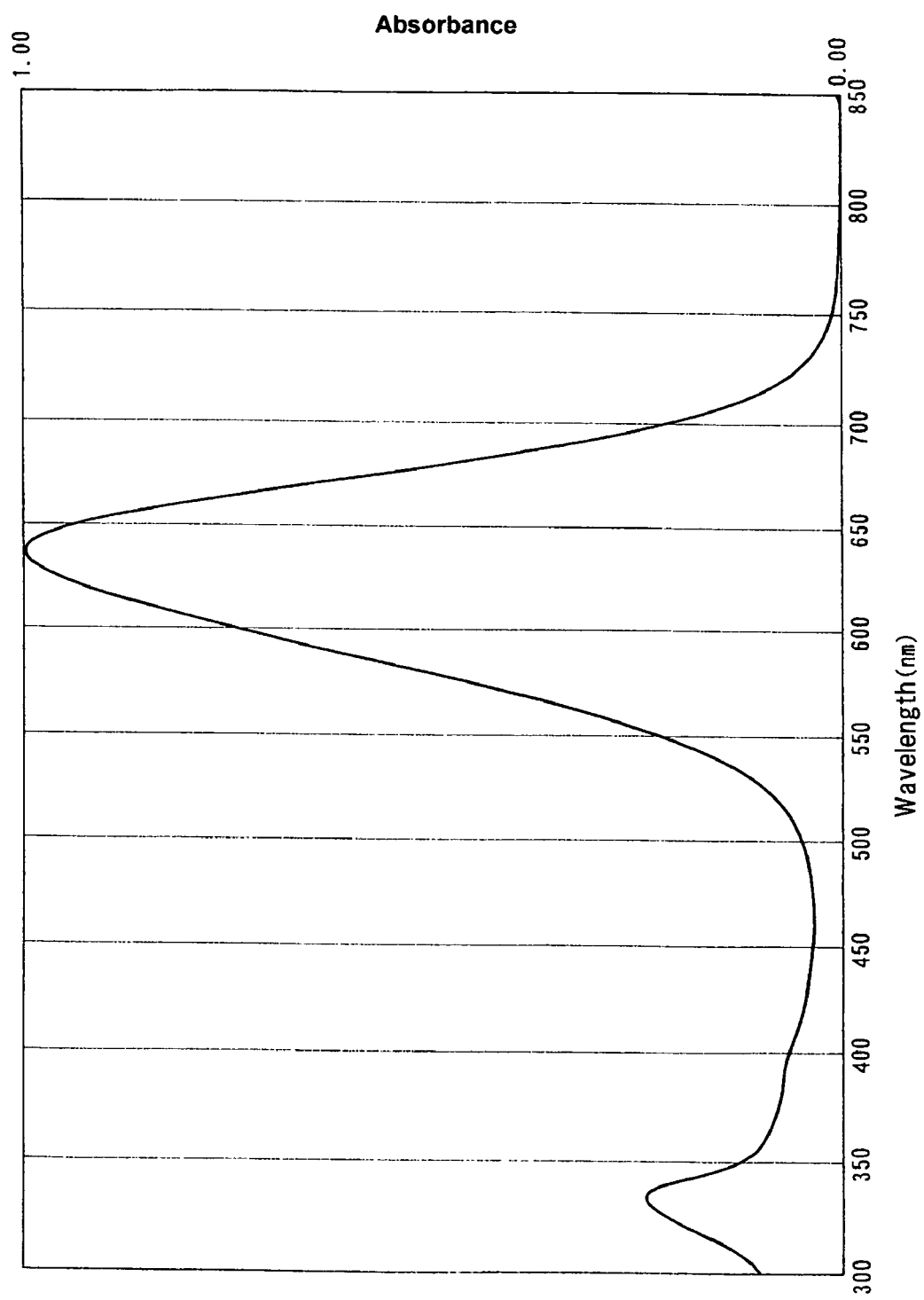
FIG. 2 is an absorption spectrum of the dye synthesized in Example 1-2 (solvent: N,N-dimethylformamide)

The obtained dye had: a melting point of 258 to 260° C., an absorption maximum λmax in DMF of 636.6 nm (ε:55,000), a pka value in DMF/water (1/1, volume ratio) of 4.1. This dye had the absorption spectrum shown in FIG. 2 and had a good hue. As to the fastness of the dye, neither a reduction in density nor discoloration was observed in the test described in Example 1 in the publication of JP-A-2000-280630; thus the dye was stable and had excellent fastness to light and heat.

Example 2-1

Synthesis of the Exemplified Compound A-29

The exemplified compound (A-29) was prepared in the following method.

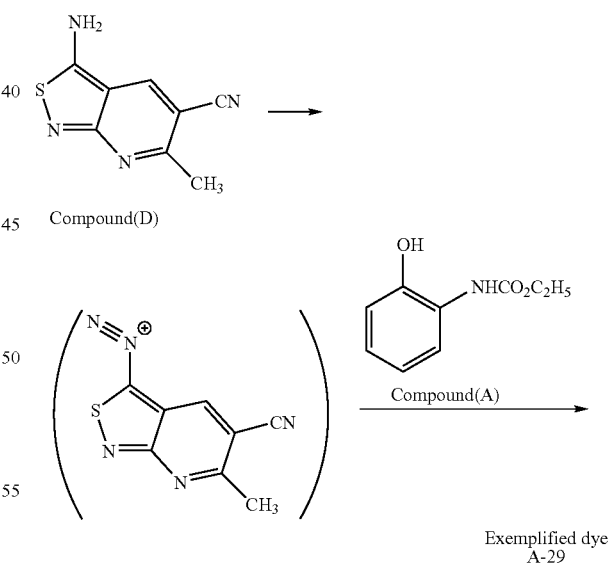

Figure 3:
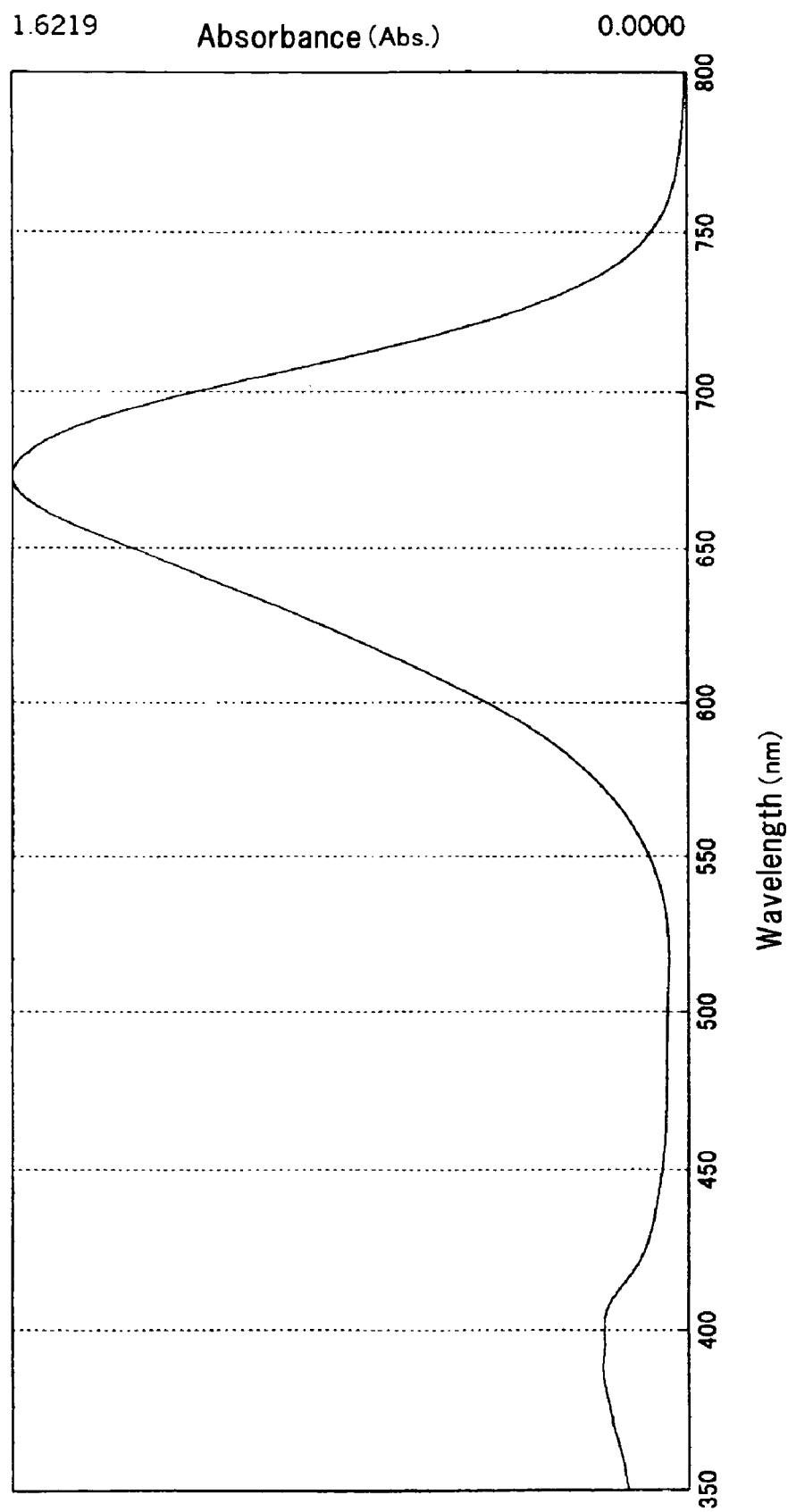
FIG. 3 is an absorption spectrum of the dye synthesized in Example 2-1.

19.0 g (0.1 mol) of the compound (D) was dissolved in 190 ml of phosphoric acid, and then 18.1 g (0.1 mol) of the compound (A) dissolved in 135 ml of acetic acid was added to the mixture. The mixture was stirred under ice-cooling. 6.9 g (0.1 mol) of sodium nitrite was added to the mixture while keeping the internal temperature of 5° C. or less, and the mixture was stirred for 120 minutes. 2 l of water was added to the reaction solution, which was then stirred for 1 hour. The precipitated crystals were collected by filtration and washed sufficiently with water. The obtained crystals were dried and purified by silica gel column chromatography. The purified crystals were subjected to crystallization using 200 ml of methanol and then subjected to filtration to collect crystals. The crystals were then washed with 50 ml of methanol, which was cooled to 10° C. or less, and dried, to obtain 8.7 g of the exemplified compound (A-29) of the present invention as reddish brown crystals. Yield: 29.9%; melting point: 215 to 217° C.; absorption λmax (absorption maximum wavelength) in DMF (N,N-dimethylformamide): 673.5 nm; ϵ (molar extinction coefficient): 66,600; pka value in DMF/water (1/1, mixing ratio in ml)): 4.98. This dye had a good hue as shown in the absorption spectrum of FIG. 3 (the abscissa: absorption wavelength, the ordinate: absorbance). As to the fastness of the dye, neither a reduction in density nor discoloration was observed in the test described in Example 1 in the publication of JP-A-2000-280630; thus the dye was stable and had excellent fastness to light and heat.

The diazo component (compound D) used in the exemplified dye A-29 can be prepared from the compound B as follows, by using the method described in the publication of JP-A-56-55455.

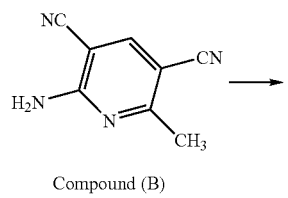

Compound (B)

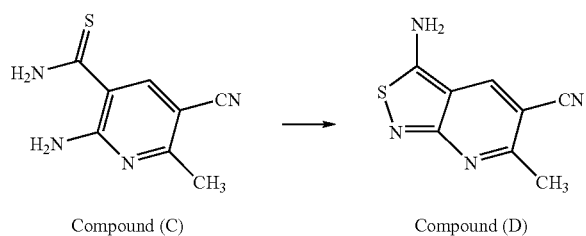

Compound (C)  Compound (D)

Example 2-2

Synthesis of the Exemplified Compound A-37

The exemplified compound (A-37) was prepared in the following method.

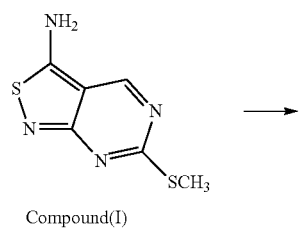

Compound(I)

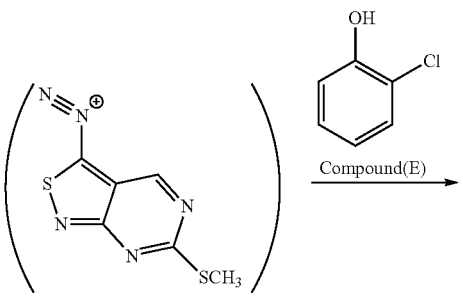

Exemplified dye A-37

Figure 4:
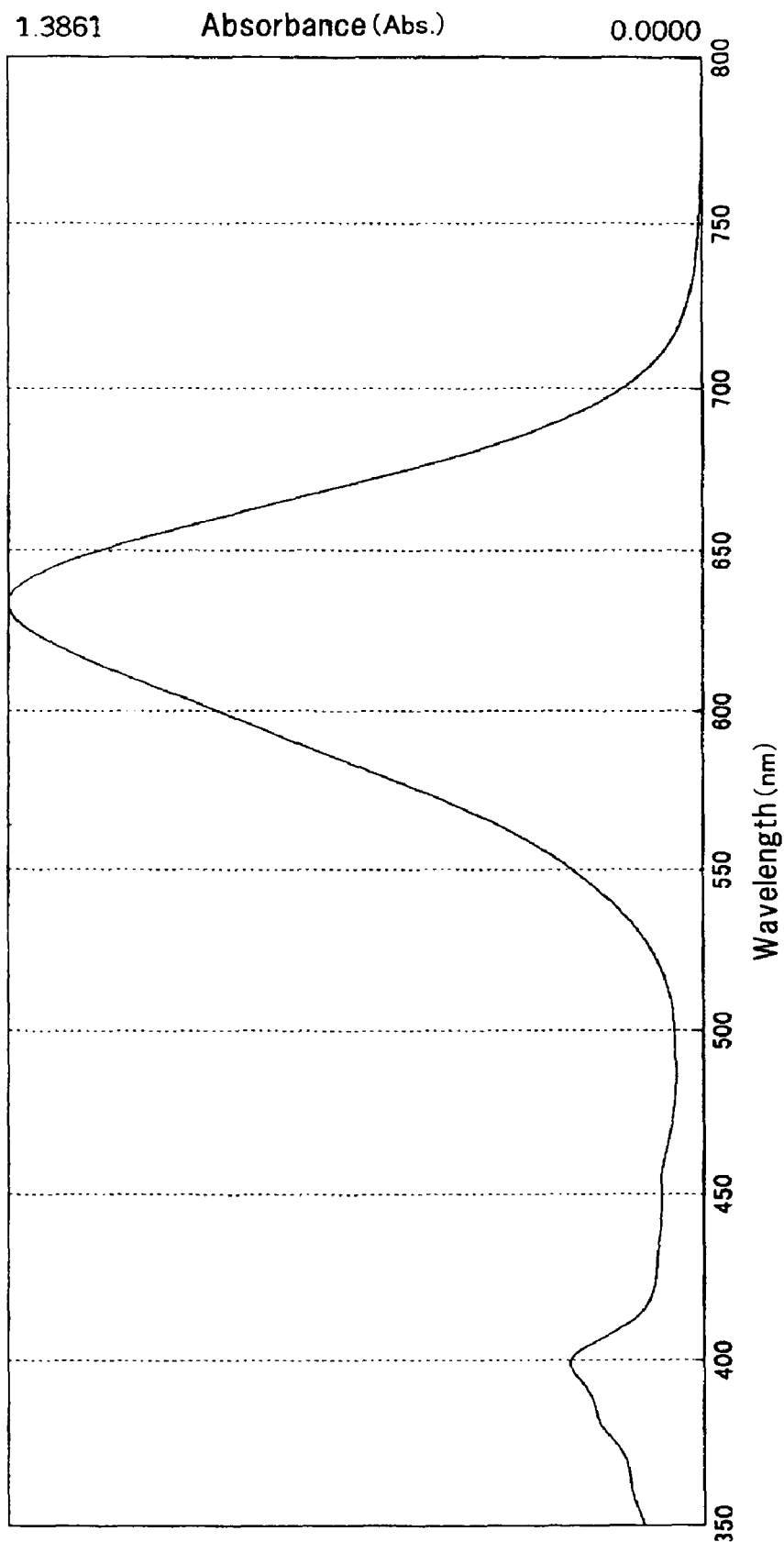
FIG. 4 is an absorption spectrum of the dye synthesized in Example 2-2.

19.8 g (0.1 mol) of the compound (I) was dissolved in 190 ml of phosphoric acid, and then 12.9 g (0.1 mol) of the compound (E) dissolved in 40 ml of acetic acid was added to the mixture. Under ice-cooling, 6.9 g (0.1 mol) of sodium nitrite was gradually added to the mixture while keeping the internal temperature of 5° C. or less, and the mixture was stirred for 120 minutes. 2 l of water was added to the reaction solution, which was then stirred for 1 hour. The precipitated crystals were collected by filtration and washed sufficiently with water. The obtained crystals were dried and purified by silica gel column chromatography. The purified crystals were subjected to crystallization using 100 ml of methanol and then subjected to filtration to collect crystals. The crystals were then washed with 50 ml of methanol, which was cooled to 10° C. or less, and dried, to obtain 9.9 g of the exemplified compound (A-37) of the present invention as reddish brown crystals. Yield: 29.3%; melting-point: 248 to 250° C.; absorption λmax in DMF: 633.6 nm; ϵ: 66,000; pka value in DMF/water (1/1, mixing ratio in ml)): 4.91. This dye had a good hue as shown in the absorption spectrum of FIG. 4. As to the fastness of the dye, neither a reduction in density nor discoloration was observed in the test described in Example 1 in the publication of JP-A-2000-280630; thus the dye was stable and had excellent fastness to light and heat.

Example 2-3

Synthesis of the Exemplified Compound A-42

The exemplified compound (A-42) was prepared in the following method.

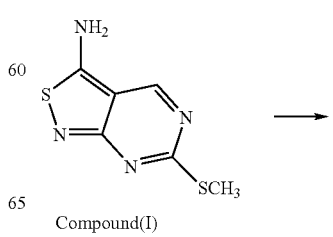

Compound(I)

43
-continued

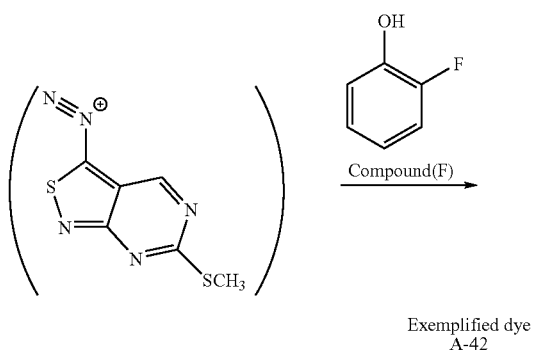

Exemplified dye
A-42

19.8 g (0.1 mol) of the compound (I) was suspended in 100 ml of phosphoric acid, and thereto 11.2 g (0.1 mol) of the compound (F) was added. Under ice cooling, 6.9 g (0.1 mol) of sodium nitrite was gradually added to the mixture while maintaining the internal temperature of 5° C. or less, and the mixture was stirred for 120 minutes. 2 l of water was added to the reaction solution, which was then stirred for 1 hour. The precipitated crystals were collected by filtration and washed sufficiently with water. The obtained crystals were dried and purified by silica gel column chromatography. The purified crystals were subjected to crystallization using 200 ml of a mixed solvent of methanol/water of 1/1 (mixing ratio in ml) and then subjected to filtration to collect crystals. The crystals were then washed with 100 ml of the aforementioned mixed solvent and dried, to obtain 8.7 g of the exemplified compound (A-42) of the present invention as reddish brown crystals. Yield: 27.1%; melting point: 240 to 241° C.; absorption λmax in DMF: 628.5 nm; ε:60,400;pka value in DMF/water of 1/1 (mixing ratio in ml): 5.02.

Figure 5:
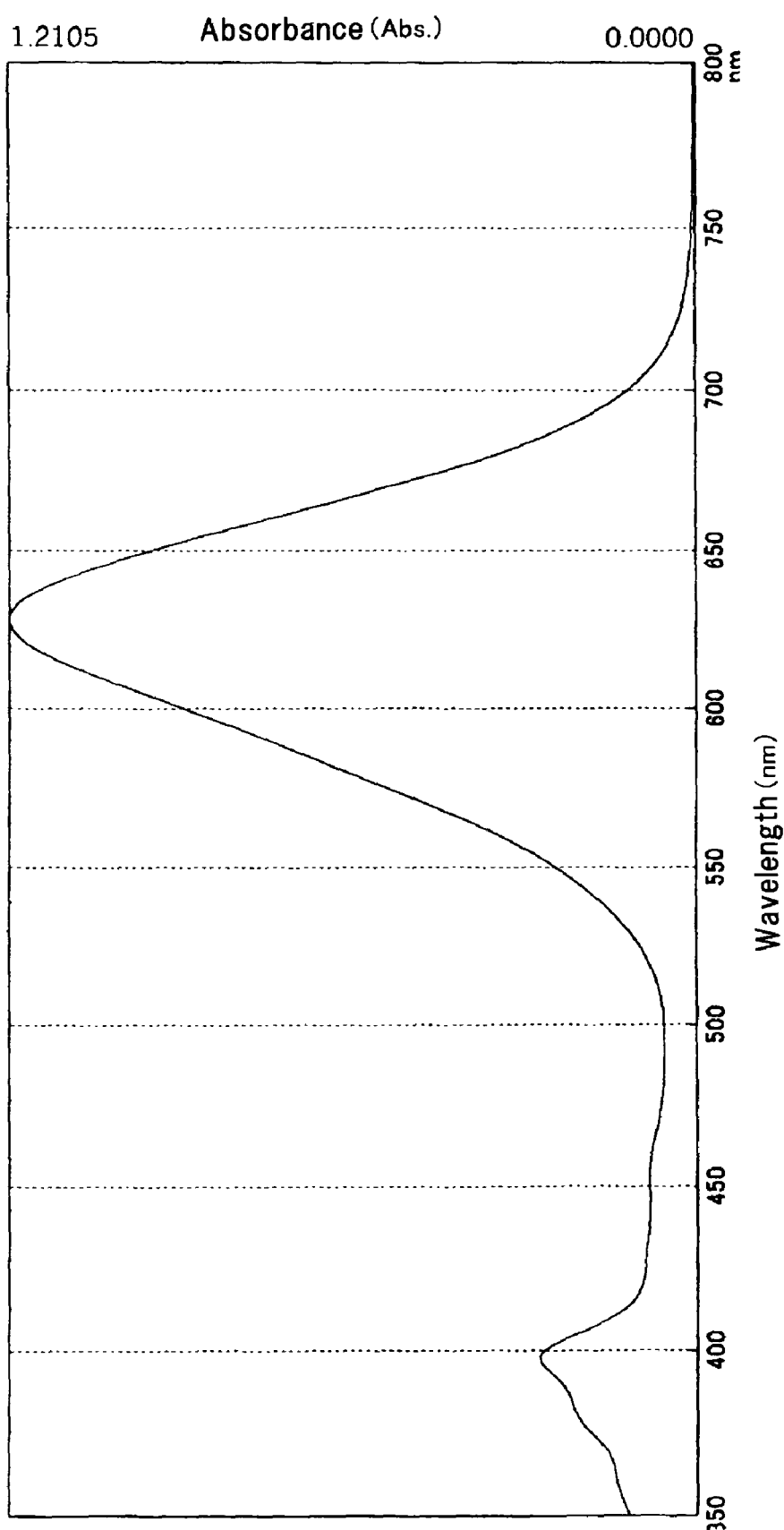
FIG. 5 is an absorption spectrum of the dye synthesized in Example 2-3.

This dye had a good hue as shown in the absorption spectrum of FIG. 5. As to the fastness of the dye, neither a reduction in density nor discoloration was observed in the test described in Example 1 in the publication of JP-A-2000-280630; thus the dye was stable and had excellent fastness to light and heat.

The diazo component (compound I) used in the synthesis of the exemplified dyes A-37 and A-42 can be prepared from the compound G as follows, by using the method described in the publication of JP-A-56-55455.

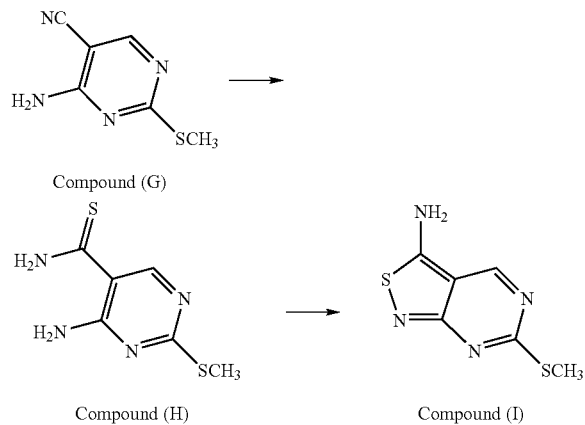

44
Example 2-4

Synthesis of the Exemplified Compound A-62

The exemplified compound (A-62) was prepared in the following method.

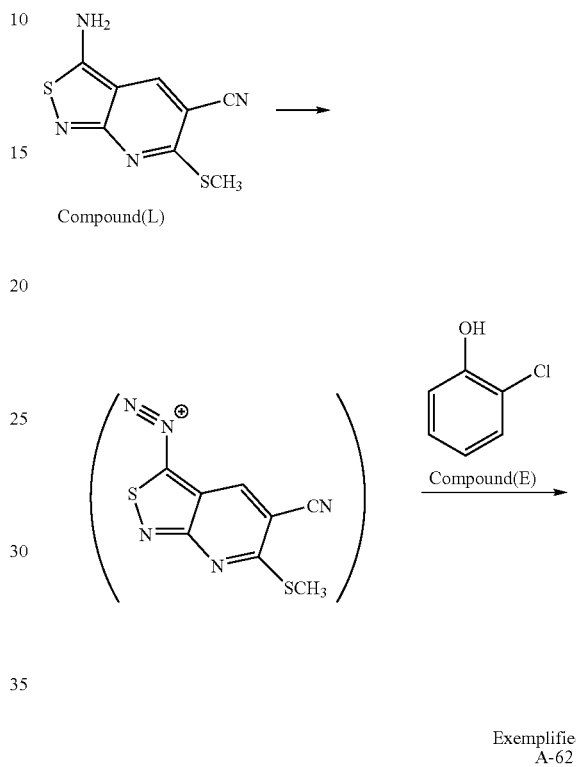

Exemplified dye
A-62

Figure 6:
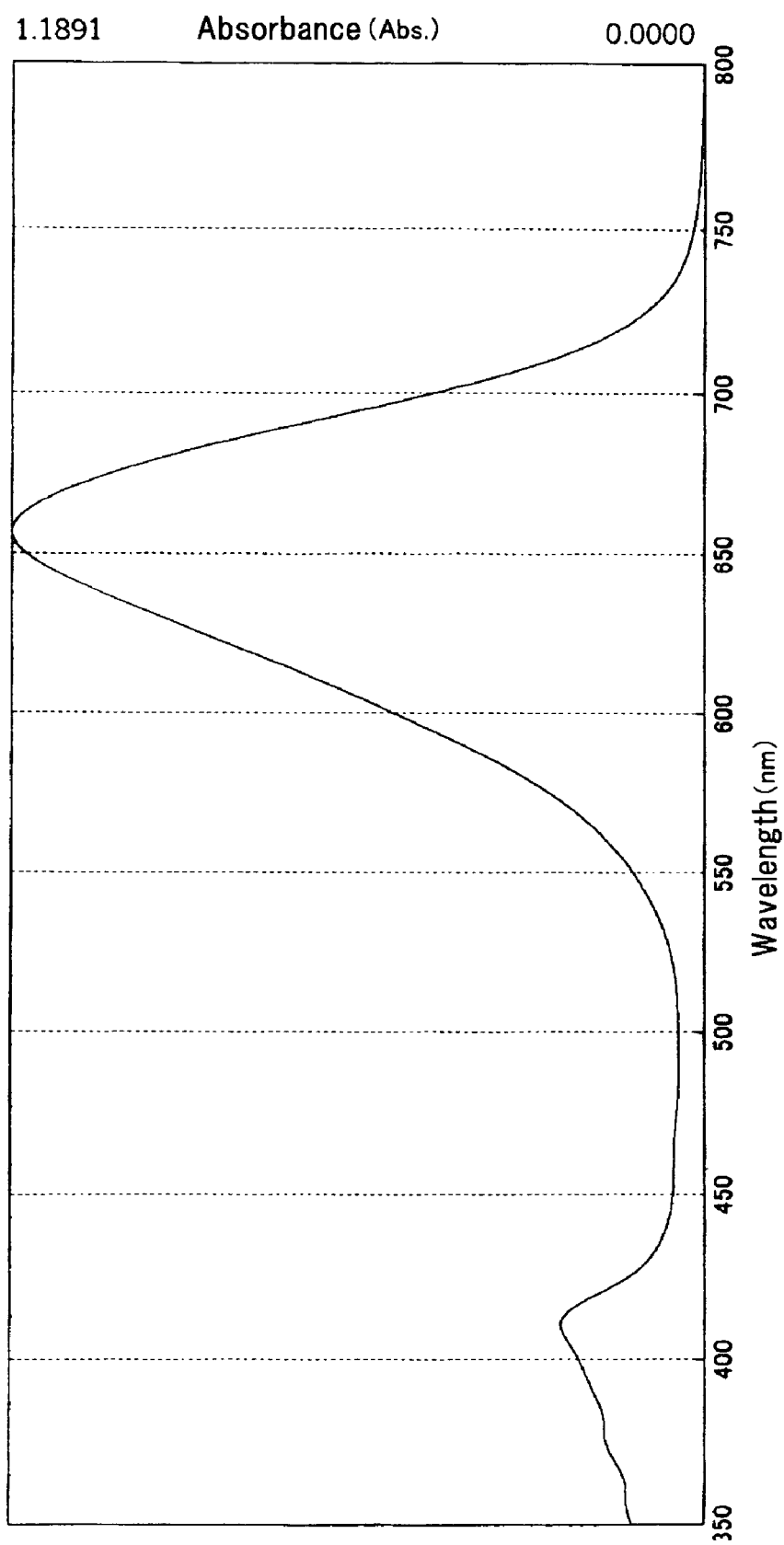
FIG. 6 is an absorption spectrum of the dye synthesized in Example 2-4.

22.2 g (0.1 mol) of the compound (L) was suspended in 100 ml of phosphoric acid and 100 ml of acetic acid, and thereto 12.9 g (0.1 mol) of the compound (E) was added. Under ice cooling, 6.9 g (0.12 mol) of sodium nitrite was gradually added to the mixture while maintaining the internal temperature of 5° C. or less, and the mixture was stirred for 120 minutes. 2 l of water was added to the reaction solution, which was then stirred for 1 hour. The precipitated crystals were collected by filtration and washed sufficiently with water. The obtained crystals were dried and purified by silica gel column chromatography. The purified crystals were subjected to crystallization using 100 ml of methanol and then subjected to filtration to collect crystals. The crystals were then washed with 100 ml of methanol and dried, to obtain 12 g of the exemplified compound (A-62) of the present invention as black crystals. Yield: 33.1%; melting point: 235 to 236° C.; absorption λmax in DMF: 656.6 nm; ε: 60,800; pka value in DMF/water=1/1 (mixing ratio in ml): 5.15. This dye had a good hue as shown in the absorption spectrum of FIG. 6. As to the fastness of the dye, neither a reduction in density nor discoloration was observed in the test described in Example 1 in the publication of JP-A-2000-280630; thus the dye was stable and had excellent fastness to light and heat.

The diazo component (compound L) used in the synthesis of the exemplified dye A-62 can be prepared from the compound J as follows, by using the method described in the publication of JP-A-56-55455.

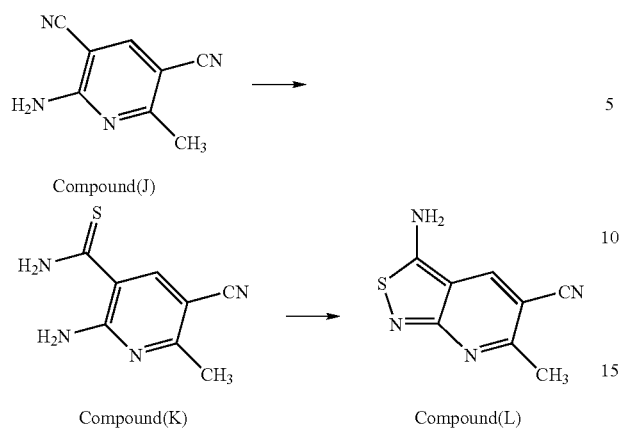

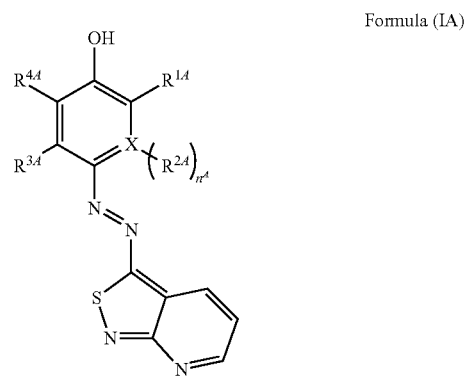

INDUSTRIAL APPLICABILITY

The azo dye (dye-stuff) represented by formula (I) may be applied in color filters for recording and reproducing a color image which filters are used in solid imaging devices such as charge-coupled devices (CCD), and CMOS and in displays such as liquid crystal displays (LCD) and plasma displays (PDP); curable compositions for producing these color filters; color image recording materials forming a color image, and dyeing applications. Specifically, the azo dye may be applied in color filters, curable compositions for producing these color filters, ink-jet-system recording materials, heat-sensitive recording materials, pressure-sensitive recording materials, recording materials for use in an electrophotographic system, transfer-type silver halide light-sensitive materials, printing inks, recording pens, and dyes for fibers. Among these, the use of the azo dye in ink-jet-system recording materials, transfer-type silver halide light-sensitive materials, and printing ink are preferable.

When the dye (dye-stuff) of the present invention is used, the properties of the dye such as solubility and dispersibility are optimized to fit to its use, by selecting a proper substituent. The dye (dye-stuff) of the present invention may be used in a solution state, an emulsion dispersion state, or a solid dispersion state, depending on the system to be used.

Having described our invention as related to the present embodiments, it is our intention that the invention not be limited by any of the details of the description, unless otherwise specified, but rather be construed broadly within its spirit and scope as set out in the accompanying claims.

The invention claimed is:

1. An azo dye represented by the following formula (IA):

Formula (IA)

wherein, in formula (IA), $R^{1A}$, $R^{2A}$, $R^{3A}$, and $R^{4A}$ each independently represent a hydrogen atom, an aliphatic group, an aryl group, a halogen atom, an acyl group, a cyano group, an acylamino group, an aliphatic oxycarbonyl group, an aryloxycarbonyl group, a carbamoyl group, an aliphatic sulfonyl group, an arylsulfonyl group, a sulfamoyl group, an aliphatic oxycarbonylamino group, an aryloxycarbonylamino group, a sulfo group, a carboxyl group, a carbamoylamino group, a sulfamoylamino group, or an aliphatic- or aromatic-sulfonylamino group, wherein $R^{1A}$ and $R^{2A}$ and/or $R^{3A}$ and $R^{4A}$ may be combined with each other to form a five- or six-membered aromatic ring or non-aromatic ring; $X^A$ represents a carbon atom or a nitrogen atom, wherein $n^A$ is 0 when $X^A$ is a nitrogen atom and $n^A$ is 1 when $X^A$ is a carbon atom.

2. The azo dye as claimed in claim 1, wherein $R^{1A}$ represents a halogen atom, a cyano group, a carbamoyl group, a sulfamoyl group, an acylamino group, an aliphatic oxycarbonyl amino group, a carbamoylamino group, an aliphatic- or aromatic-sulfonylamino group, or a sulfamoylamino group.

3. The azo dye as claimed in claim 1, wherein $R^{2A}$ represents a halogen atom, a hydrogen atom, or an aliphatic group.

4. The azo dye as claimed in claim 1, wherein $R^{3A}$ represents a hydrogen atom, a halogen atom, an acylamino group, an aliphatic oxycarbonylamino group, a carbamoylamino group, an aliphatic- or aromatic-sulfonylamino group, or a sulfamoylamino group.

5. The azo dye as claimed in claim 1, wherein $R^{4A}$ represents a halogen atom, a hydrogen atom, or an acylamino group.

6. The azo dye as claimed in claim 1, wherein $X^A$ is a carbon atom.

* * * * *